(12) United States Patent
Padua et al.

(10) Patent No.: US 7,381,710 B2
(45) Date of Patent: Jun. 3, 2008

(54) COMBINED DNA VACCINE AND BIOLOGICAL MODIFIERS FOR CANCER THERAPY

(75) Inventors: Rose Ann Padua, London (GB); Christine Chomienne, Paris (FR); Dominique Charron, Paris (FR)

(73) Assignee: Institut National de la Sante et de la Recherche Medicale, Paris (FR)

( * ) Notice: Subject to any disclaimer, the term of this patent is extended or adjusted under 35 U.S.C. 154(b) by 0 days.

(21) Appl. No.: 10/512,475

(22) PCT Filed: Apr. 24, 2003

(86) PCT No.: PCT/IB03/01600

§ 371 (c)(1),
(2), (4) Date: Aug. 15, 2005

(87) PCT Pub. No.: WO03/090778

PCT Pub. Date: Nov. 6, 2003

(65) Prior Publication Data

US 2006/0079470 A1    Apr. 13, 2006

(30) Foreign Application Priority Data

Apr. 26, 2002  (EP) ................................ 02291069

(51) Int. Cl.
  *A01N 43/04*    (2006.01)
  *A01N 63/00*    (2006.01)
  *A61K 31/70*    (2006.01)
  *A61K 48/00*    (2006.01)

(52) U.S. Cl. ..................... 514/44; 424/93.2; 424/93.21

(58) Field of Classification Search .................. 514/44; 435/320.1; 424/93.2, 93.1
See application file for complete search history.

(56) References Cited

U.S. PATENT DOCUMENTS 6,156,316 A * 12/2000 Scheinberg et al. ....... 424/185.1

FOREIGN PATENT DOCUMENTS

WO        WO 95/04151     *  2/1995

OTHER PUBLICATIONS

Le et al. Recombinant PML Adenovirus Suppresses Growth and Tumroigenicity of Human Breast Cancer Cells by Inducing G1 Cycle Arrest and Apoptosis. Oncogene. 1998, vol. 16, pp. 1839-1849.*
Pandolfi et al. Structure and Origin of the Acute Promyelocytic Leukemia myl/RARAlpha cDNA and Characterization of its Retinoid-Binding and Transactivation Properties. Oncogene. 1991, vol. 6, pp. 1285-1292.*
Grignani et al. Acute Promyelocytic Leukemia: From Genetics to Treatment. Blood. 1994, Jan. 1, 1994, pp. 10-25.*

* cited by examiner

*Primary Examiner*—Deborah Crouch
(74) *Attorney, Agent, or Firm*—B. Aaron Schulman; Stites & Harbison PLLC

(57) ABSTRACT

The present invention relates to the combination of a DNA vaccination strategy that makes use of a nucleic acid encoding an immunogenic polypeptide, with a non-immunosuppressive inducer of tumor cell differentiation and/or apoptosis or a tumor cell modifier, useful for cancer therapy. Vaccine compositions and kits are provided, as well as specific nucleic acid constructs that are particularly suitable for the preparation of such compositions.

7 Claims, 9 Drawing Sheets

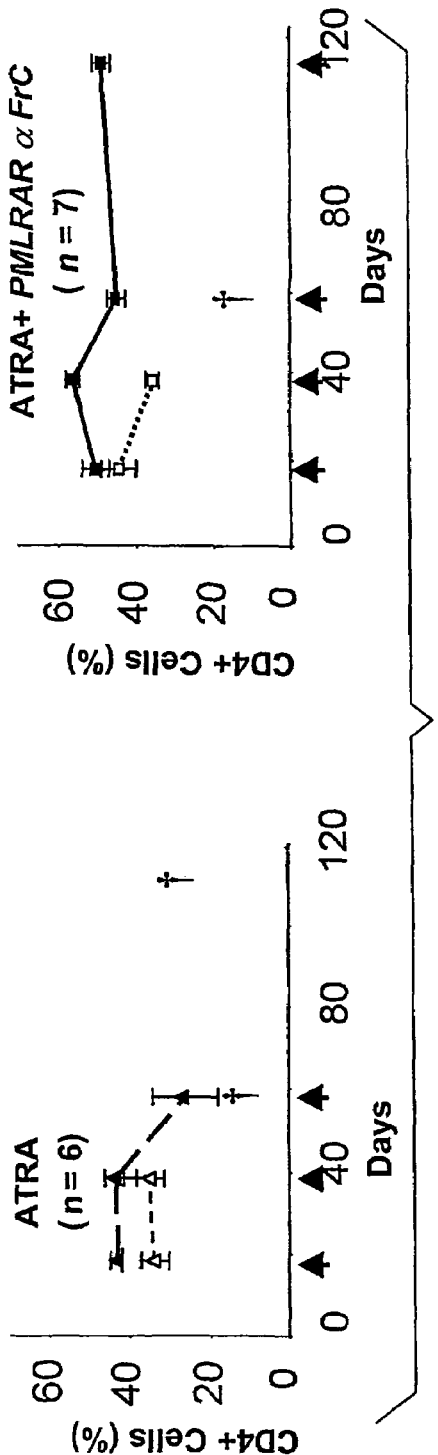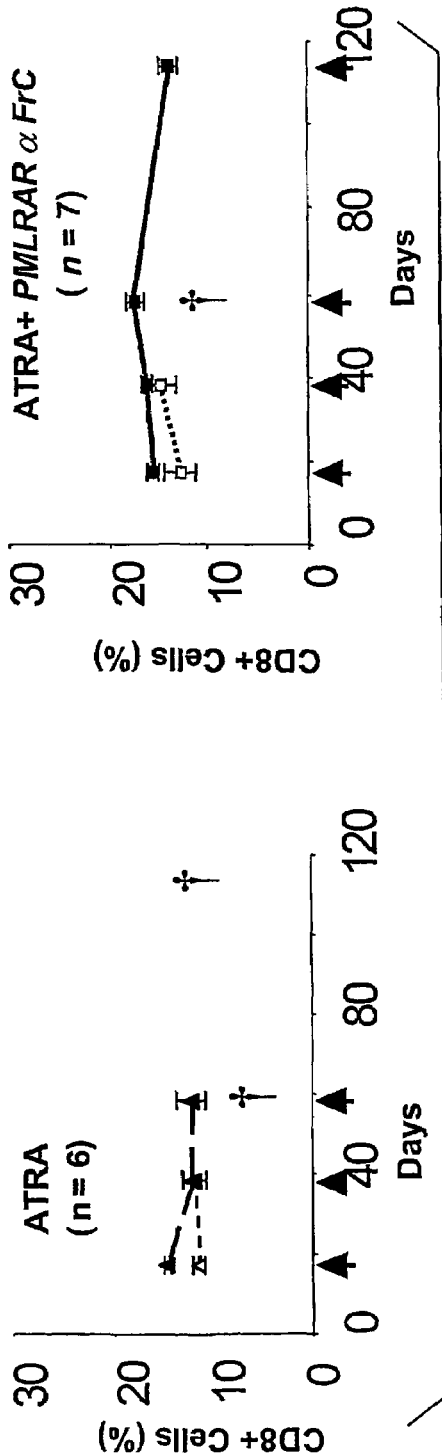
FIG.5A
FIG.5B

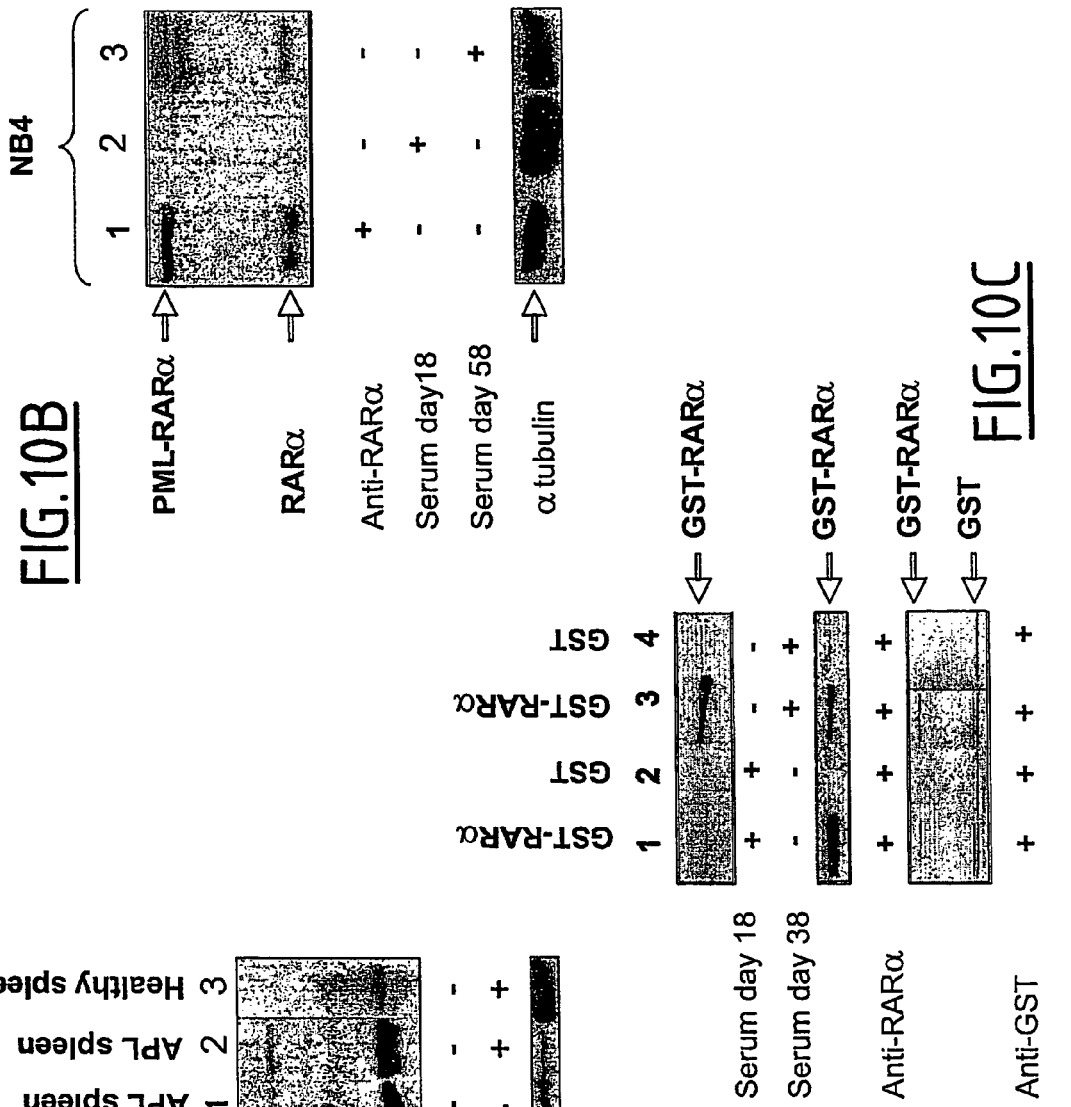
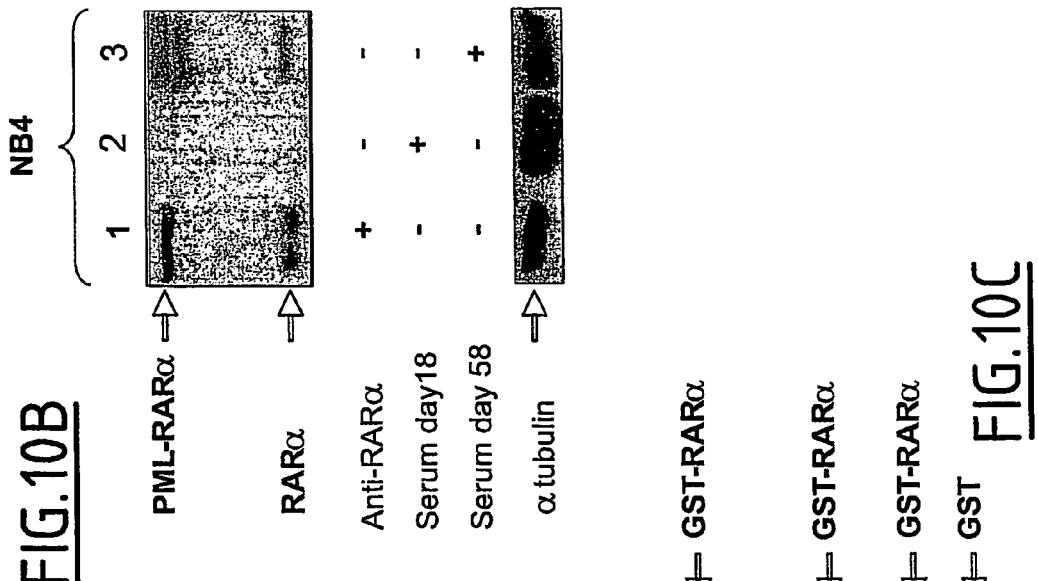
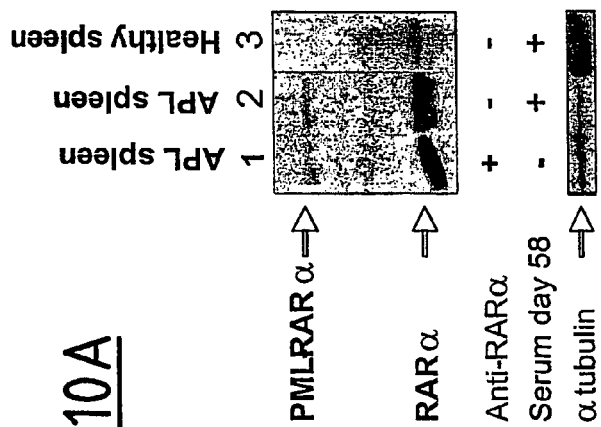
FIG. 10A
FIG. 10B
FIG. 10C
FIG. 10

COMBINED DNA VACCINE AND BIOLOGICAL MODIFIERS FOR CANCER THERAPY

The present invention relates to the combination of a DNA vaccination strategy that makes use of a nucleic acid encoding an immunogenic polypeptide, in particular a tumor antigen, with a non-immunosuppressive inducer of tumor cell apoptosis, useful for cancer therapy.

To date, many tumor-associated antigens have been identified and vaccination strategies to elicit immune response against these tumor antigens have been developed. Natural and recombinant cancer protein antigens contain defined immunogenic antigens at standardized levels and their efficacy depends on finding the right adjuvant and delivery system. DNA delivery, e.g. direct injection of gene expression cassettes into a living host, is a novel approach to vaccine and immune therapy. Expression of the delivered genes may result in the specific immune activation of the host immune defenses against the expressed antigen.

The effectiveness of a vaccine strategy relies on the acquisition of an immune response that can be both humoral and cytotoxic. DNA vaccines have been shown to meet these requirements, leading to a strong and persistent cell-mediated (generation of CD8+ cytotoxic and CD4+ helper T cells) and humoral immune responses to the antigen encoded by the plasmid. The application of this type of vaccination to cancers was used first on B-NHL using the idiotype of the surface immunoglobulin as the antigen against which the anti-tumoral response was elicited (Stevenson, F. K. et al., 1995; Syrengelas, A. D. et al., 1996). The protective immunity was also observed in other mouse models of lymphoma and myeloma.

Acute promyelocytic leukemia (APL) is characterized by a reciprocal t(15;17) translocation fusing the Promyelocytic Leukemia gene (PML) to the retinoic acid receptor alpha gene (RARα), and by an arrest of myeloid differentiation at the promyelocytic stage. All-trans retinoic acid (ATRA) mediated differentiation therapy is now the basis of standard treatment in patients with APL. However, despite prolonged survival obtained with the current trials combining ATRA with chemotherapy, around 10 to 20% of patients still relapse. Therefore, novel therapeutic strategies to eradicate residual disease are needed.

It has been shown that PML-RARα junction peptides can be specifically recognized by CD4 T-lymphocytes (Dermime, S. et al., 1996). However, this approach was limited as no peptide specific T-cell line or clone could be generated from cells of patients with APL. This result is ascribed to the generalized impairment of the cellular immune system already reported in cancer patients. On this account, the poor immune status of APL patients is regarded as a major obstacle for immunotherapeutic approaches to APL.

The inventors' collaborators previously developed transgenic mice expressing a human PML-RARα cDNA that provide an accurate animal model for human APL (Brown, D. et al., 1997). The inventors took advantage of this APL animal model to test the in vivo efficacy of a newly developed PML-RARα DNA based vaccine linked to tetanus toxin fragment C (FrC) sequences. Surprisingly, their results demonstrate that ATRA acts as an adjuvant with PML-RARα-FrC DNA vaccination to prolong survival. This was accompanied by an increase in CD4+ and CD8+ T-cells, RARα antibody and IFNγ production, suggesting the induction of relevant immune responses. When high dose of ATRA is administered, antibodies directed against FrC are also detected. Therefore, a particular subject of the present invention is a vaccine composition that comprises a nucleic acid PML (Promyelocytic Leukemia gene)—RARα (retinoic acid receptor alpha gene)—FrC (tetanus toxin fragment C) fusion gene and all-trans retinoic acid (ATRA) that induces protective immunity and extends lifespan in an acute promyelocytic leukemia animal model.

More generally these results provide a novel targeted approach for APL therapy and may improve clinical outcome in human APL, by combining a DNA vaccination with conventional ATRA therapy.

Furthermore, the inventors found the ability of the DNA that contains a PML-RARα-FrC gene to induce protection against challenge encouraging, and led them contemplate other oncogenic fusions. The inventors have shown indeed, for the first time, that the adjuvant property of the combination of ATRA and a strongly immunogenic DNA sequence may help maintain clinical remissions by boosting immune responses against tumor antigens generated by patients.

The inventors have further shown the ability of a DNA that contains a non-specific immunogenic sequence fused to a sequence encoding a polypeptide which enhances the immune response, such as a PML-RARαAS-FrC or ScFvBCL1-FrC sequence, combined with ATRA to induce protection against challenge.

The present invention thus provides a vaccine composition comprising (i) a non-immunosuppressive inducer of tumor cell apoptosis and (ii) a nucleic acid comprising a sequence that encodes an immunogenic polypeptide, in particular a tumor antigen, in a pharmaceutically acceptable carrier. Said nucleic acid comprising a polynucleotide encoding an immunogenic polypeptide is present in an amount effective to suppress or attenuate tumor growth upon administration to a mammal, in particular to a human.

Definitions

In the context of the present invention, a "nucleic acid" refers to the phosphate ester polymeric form of ribonucleosides ("RNA molecules") or deoxyribonucleosides ("DNA molecules"), or any phosphoester analogs thereof, such as phosphorothioates and thioesters, in either single stranded form, or a double-stranded helix. The term "nucleic acid" includes double-stranded DNA round, inter alia, in linear (e.g., restriction fragments) or circular DNA molecules.

The present invention makes use of nucleic acids (or polynucleotides) that encode for immunity-conferring polypeptides (in other words immunogenic polypeptides), such as tumor associated antigens. Such polypeptides can then act as immunogens to provoke a humoral or cellular response, or both. In the context of the invention, the immunogenic polypeptide may be "specific" of a disease condition, such as a tumor associated antigen, or "non-specific", such as a polypeptide encoded by an antisense sequence, for instance an antisense of a tumor antigen, or an immunogenic polypeptide that has no relevance with regards to the disease condition. Such irrelevant immunogenic polypeptides include for instance a ScFv protein unique to a lymphoma patient (pScFvBcl1FrC, King et al., 1998) whereas the disease is leukaemia.

The immunogenic polynucleotide sequences, and in particular the tumor antigen polynucleotide sequences, may be used in association with other polynucleotide sequences coding for regulatory proteins that control the expression of the immunogenic (tumor antigen) sequence. The nucleic acid according to the invention may additionally contain recognition and promoter sequences. Advantageously the nucleic acid is a vector, such as a plasmid.

The nucleic acids used in the compositions of the invention can be "naked" materials. A "naked" nucleic acid material means that it is free from any delivery vehicle that can act to facilitate entry into the cell. For example, the polynucleotide sequences are free of viral sequences, particularly any viral particles that may carry genetic information. A pharmaceutical product comprising naked polynucleotide for vaccination is described in EP 0465529.

As used herein, two nucleic acid sequences that are "operatively linked" are placed under the control of an expression control sequence that controls and regulates the transcription and translation of both nucleic acid sequences.

As used herein, sequences that are "fused in frame" refers to sequences that form a hybrid gene thereby encoding a fusion polypeptide. A fusion polypeptide is one that contains an immunogenic polypeptide, and more specifically a tumor antigen of the invention, fused at the N or C-terminal end to any other polypeptide. A preferred example of a fusion polypeptide is one where the immunogenic polypeptide, such as a tumor antigen, is fused to a polypeptide having adjuvant activity, such as tetanus toxin fragment C. For example, the fusion of tetanus toxin fragment C to a tumor antigen promotes the immune response elicited by the tumor antigen.

The cloning and sequencing of the structural gene for tetanus toxin have been described in Fairweather et al. (1986) and Fairweather and Lyness (1986) (SEQ ID no9). Fragment C (FrC) is a 50 kD polypeptide generated by papain cleavage of the toxin and comprises the 451 amino acids at the C-terminus.

A "PML-RARα antigen" denotes a fusion protein resulting from the t(15;17) chromosomal translocation described in Thé et al. (1990), which encompasses the most common bcr 1 breakpoint of 3 so far described. Examples of PML-RARα antigens are encoded by polynucleotides comprising the sequence SEQ ID no1 or derivative thereof, provided that the PML/RARα junction is recognized by the immune system of the patient.

"PML-RARαAS" denotes a polypeptide encoded by a sequence complementary to the sequence SEQ ID no1, or a fragment thereof spanning the PML-RARα fusion point. Preferably, PML-RARαAS is encoded by the sequence shown in SEQ ID no8.

"Derivatives" include sequence-conservative variants and function-conservative variants. "Sequence-conservative variants" of a polynucleotide sequence are those in which a change of one or more nucleotides in a given codon position results in no alteration in the amino acid encoded at that position. "Function-conservative variants" are polynucleotide sequences that code for proteins wherein at least one given amino acid residue has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art.

"Adjuvant" activity is defined herein as an effect achieved by the combination of two components that is greater than the effect of either of the two components alone. This synergistic effect is particularly apparent when the effect of DNA vaccination and ATRA alone are compared to the combined effect. ATRA or vaccine alone still result in relapse and death in all animals, whereas their combination results in effective cure in 50% of the animals treated.

A "pharmaceutically acceptable carrier" refers to any vehicle wherein the vaccine compositions according to the invention, or nucleic acids and kits, may be formulated. It includes a saline solution such as phosphate buffer saline. In general, a diluent or carrier is selected on the basis of the mode and route of administration, and standard pharmaceutical practice.

"Apoptosis" refers to a form of cell death that exhibits stereotypic morphological changes as reviewed in Raff (1998). Apoptosis can be measured, e.g., by the propidium iodide flow cytometry assay described in Dengler et al. (1995), or by the in situ terminal deoxynucleotidyl transferase and nick translation assay (TUNEL analysis) described in Gorczyca (1993).

"Arsenic related compounds" denotes any compound that, just as arsenic, is a phosphatase inhibitor or is capable of creating covalent bonds by dithiol group binding.

Vaccine Compositions

The vaccine compositions according to the invention comprise a nucleic acid that encodes an immunogenic polypeptide and optionally a nucleic acid that encodes a polypeptide that enhances the immune response. According to a particular embodiment, the sequence that encodes an immunogenic polypeptide and the sequence that encodes a polypeptide that enhances the immune response are operatively linked, preferably fused in-frame.

Advantageously, the sequence that encodes a polypeptide that enhances the immune response is selected from the group consisting of a tetanus toxin sequence, preferably the fragment C (FrC) sequence, the cholera toxin (CT) sequence, the *E. coli* heat-labile toxin (LT) sequence, the *Clostridium difficile* toxin A sequence and the pertussis toxin (PT) sequence, or fragments, homologs, derivatives, and fusions to any of these toxins are also suitable, provided that they retain adjuvant activity.

According to a first embodiment, the immunogenic polypeptide may be "non-specific" of a cancer condition. Advantageously, the sequence that encodes said immunogenic polypeptide may be selected from the sequences PML-RARαAS-FrC (SEQ ID no10) or ScFvBCL1-FrC (SEQ ID no11).

"PML-RARαAS-FrC" denotes the PML-RARαAs sequence which has been cloned in frame to a BCL1 leader sequence at the 5' position and to the whole of fragment C at the 3' position (SEQ ID no10).

"ScFvBCL1-FrC", also called BCL1-Frc in the figure, denotes the ScFv construct disclosed in King et al 1998 that has been cloned from a lymphoma patient fused in frame to a BCL1 leader sequence at the 5' position and to the whole of fragment C at the 3' position (SEQ ID no11).

Any immunogenic sequence comprising a FrC sequence, or any equivalent immune response enhancer, even though the sequence does not include a tumor antigen, may be appropriate. The scope of this embodiment should not be limited to the sole PML-RARαAS-FrC and ScFvBCL1-FrC sequences described above.

In another embodiment, the immunogenic polypeptide may comprise a tumor antigen. Thus, according to this embodiment, the vaccine compositions of the invention comprise a nucleic acid that codes for a tumor antigen.

Among tumor antigens that can be advantageously used, one can cite human PML (Promyelocytic Leukemia gene)—RARα (retinoic acid receptor alpha gene), acute myeloid leukemia 1/Eight-Twenty one (AML1/ETO), core binding factor beta/muscle myosin heavy chain (CBF beta/MYH11), ets-like gene/plaletet derived growth factor receptor beta (Tel-PDGF), promyelocytic leukemia zing finger/retinoic acid receptor alpha (PLZF-RAR), myeloid/lymphoid (MLL) fusions, of which there are 40 potential partners, ets-like gene/acute myeloid leukemia 1 (TEL/AML-1), breakpoint cluster region/Abelson (BCR/ABL) (Yun et al., 1999). In a particular aspect of the invention, the tumor antigen is PML-RARα. Accordingly, the polynucleotide encoding a tumor antigen of the vaccine composition may comprise sequence SEQ ID no1 (PML-RARα fusion point):

5'-gag gtc ftc ctg ccc aac agc aac cac gtg gcc agt ggc gcc ggg gag gca g←PML|RAR→cc aft gag acc cag agc agc agt tct gaa gag ata gtg ccc agc cct ccc tcg-3'.

When the immunogenicity of the sole tumor antigen is not sufficient to insure efficient protection against tumor growth, it may be desired to provide a nucleic acid sequence that encodes a polypeptide that enhances the immune response to the tumor antigen. Such nucleic acid sequence may be carried on different nucleic acids or on a same nucleic acid.

The vaccine composition may thus further comprise a nucleic acid comprising a sequence that encodes a polypeptide that enhances the immune response to the tumor antigen. Alternatively the nucleic acid that encodes a tumor antigen may further comprise a sequence that encodes a polypeptide that enhances the immune response to the tumor antigen. According to a particular embodiment, the polynucleotide sequence encoding a tumor antigen and the polynucleotide sequence encoding a polypeptide that enhances the immune response to the tumor antigen are operatively linked, preferably fused in-frame.

The nucleic acid comprising a polynucleotide encoding a polypeptide which enhances the immune response to the tumor antigen may be advantageously selected from the group consisting of a tetanus toxin sequence, preferably the fragment C (FrC) sequence, the cholera toxin (CT) sequence, the *E. coli* heat-labile toxin (LT) sequence, the *Clostridium difficile* toxin A sequence and the pertussis toxin (PT) sequence, or fragments, homologs, derivatives, and fusions to any of these toxins are also suitable, provided that they retain adjuvant activity.

Preferably, the nucleic acid used in the composition of the invention comprises a sequence that encodes a PML-RARα-FrC antigen (SEQ ID no2 or 7).

The vaccine composition of the invention advantageously comprises a non-immunosuppressive inducer of tumor cell apoptosis or a non-immunosuppressive tumor cell modifier that has adjuvant activity towards the biological response elicited by said nucleic acid encoding the tumor antigen.

Preferably the non-immunosuppressive inducer of tumor cell apoptosis may be selected either from differentiation inducers or selected from the group consisting of arsenic and arsenic related compounds (Lallemand-Breitenbach et al., 1999), all-trans retinoic acid and other retinoid compounds which induce differentiation and apoptosis such as 9-cis RA N-(4-hydroxyphenyl)retinamide (4 HPR), 13 cis RA. CD437 and other differentiation and apoptosis inducers, activation of CD44 by antibodies or hyaluronic acid, hematopoietic growth and differentiation factors may also be effective.

The vaccine composition of the invention allows the simultaneous administration of a non-immunosuppressive inducer of tumor cell apoptosis and of a nucleic acid comprising a sequence that encodes an immunogenic polypeptide, in particular a tumor antigen. However this combined therapy may also be achieved by simultaneously or sequentially administering a composition comprising a non-immunosuppressive inducer of tumor cell apoptosis, and a composition comprising a tumor antigen encoding nucleic acid.

For that purpose the compositions may be in the form of a kit.

Kits

The present invention thus provides a kit comprising (i) a first pharmaceutical composition that comprises a non-immunosuppressive inducer of tumor cell apoptosis and (ii) a second pharmaceutical composition that comprises a nucleic acid comprising a sequence that encodes an immunogenic polypeptide, and preferably a tumor antigen.

The present invention also provides a kit comprising (i) a first pharmaceutical composition that comprises a non-immunosuppressive inducer of tumor cell apoptosis and (ii) a second pharmaceutical composition that comprises a nucleic acid comprising a sequence that encodes an immunogenic polypeptide, preferably a tumor antigen, fused in-frame or linked to a sequence that encodes a polypeptide that enhances the immune response.

The nucleic acid and the non-immunosuppressive inducer of tumor cell apoptosis are as defined above. Preferably, the inducer has adjuvant activity towards the biological response elicited by the nucleic acid that encodes the immunogenic polypeptide, and in particular the tumor antigen. It may be selected from the group consisting of arsenic, all-trans retinoic acid, 9-cis RA, 4 HPPR, 13 cis RA, CD437 and other differentiation and apoptosis inducers, antibodies or hyaluronic acid, hematopoietic growth and differentiation factors.

The components of the kit are preferably formulated in pharmaceutically acceptable carriers.

The nucleic acid and the non-immunosuppressive inducer of tumor cell apoptosis may be administered concurrently, i.e. simultaneously in time, or sequentially, i.e. at different times during the course of a common treatment schedule.

Specific Nucleic Acids

Specific isolated nucleic acids useful in the compositions and kits of the invention are also part of the present invention.

A particular subject of the invention is an isolated nucleic acid that comprises (a) a sequence encoding a PML-RARα antigen and further comprises (b) a sequence encoding a polypeptide that enhances the immune response to said PML-RARα antigen.

In a preferred embodiment, the sequence encoding a PML-RARα antigen and the sequence encoding a polypeptide that enhances the immune response to the PML-RARα antigen are operatively linked. Still preferably, said polynucleotides are fused in-frame. Preferably the sequence of the polynucleotide that encodes a PML-RARα antigen is SEQ ID no1.

Advantageously, the sequence that encodes a polypeptide that enhances the immune response to the PML-RARα antigen is selected from the group consisting of a tetanus toxin sequence, preferably the fragment C (FrC) sequence, the cholera toxin (CT) sequence, the *E. coli* heat-labile toxin (LT) sequence, the *Clostridium difficile* toxin A sequence and the pertussis toxin (PT) sequence, or fragments, homologs, derivatives, and fusions to any of these toxins are also suitable, provided that they retain adjuvant activity. The isolated nucleic acid of the invention may thus comprise sequence SEQ ID no 2 or SEQ ID no 7).

Non-Specific Nucleic Acids

Non-specific isolated nucleic acids useful in the compositions and kits of the invention are also part of the present invention.

A particular subject of the invention is an isolated nucleic acid that comprises (a) a sequence encoding an immunogenic polypeptide, such as PML-RARαAS, and further comprises (b) a sequence encoding a polypeptide that enhances the immune response to said immunogenic polypeptide.

In a preferred embodiment, the sequence encoding an immunogenic polypeptide and the sequence encoding a polypeptide that enhances the immune response to the immunogenic polypeptide are operatively linked. Still preferably, said polynucleotides are fused in-frame. Preferably, the sequence of the polynucleotide that encodes PML-RARαAS is SEQ ID no8.

Advantageously, the sequence that encodes a polypeptide that enhances the immune response to the immunogenic polypeptide is selected from the group consisting of a tetanus toxin sequence, preferably the fragment C (FrC) sequence, the cholera toxin (CT) sequence, the E. coli heat-labile toxin (LT) sequence, the Clostridium difficile toxin A sequence and the pertussis toxin (PT) sequence, or fragments, homologs, derivatives, and fusions to any of these toxins are also suitable, provided that they retain adjuvant activity. The isolated nucleic acid of the invention may thus comprise a sequence encoding a PML-RARαAS-FrC polypeptide as shown in the sequence SEQ ID no10.

Therapeutics

The nucleic acids as defined according to the invention may be administered in a naked form, free from any delivery vehicles. To this end, the nucleic acid is simply diluted in a physiologically acceptable solution such as sterile saline or sterile buffered saline, with or without a carrier. When present, the carrier preferably is isotonic, hypotonic, or weakly hypertonic, and has a relatively low ionic strength, such as provided by a sucrose solution, e.g., a solution containing 20% sucrose.

Alternatively, the isolated nucleic acid or the nucleic acid of the vaccine compositions or kits of the invention may be administered in association with agents that assist in cellular uptake. Examples of such agents are (i) chemicals that modify cellular permeability, such as bupivacaine (see, e.g., WO 94/16737), (ii) liposomes or viral particles for encapsulation of the polynucleotide, or (iii) cationic lipids or silica, gold, or tungsten microparticles which associate themselves with the polynucleotides.

Anionic and neutral liposomes are well-known in the art (see, e.g., Liposomes: A Practical Approach, RPC New Ed, IRL press (1990), for a detailed description of methods for making liposomes) and are useful for delivering a large range of products, including polynucleotides.

Cationic lipids are also known in the art and are commonly used for gene delivery. Such lipids include Lipofectin™ also known as DOTMA (N-[I-(2,3-dioleyloxy) propyls N,N, N-trimethylammonium chloride), DOTAP (1,2-bis (oleyloxy)-3 (trimethylammonio) propane), DDAB (dimethyldioctadecyl-ammonium bromide), DOGS (dioctadecylamidologlycyl spermine) and cholesterol derivatives such as DCChoi (3 beta-(N-(N',N'-dimethyl aminomethane)-carbamoyl) cholesterol). A description of these cationic lipids can be found in EP 187,702, WO 90/11092, U.S. Pat. No. 5,283,185, WO 91/15501, WO 95/26356, and U.S. Pat. No. 5,527,928. Cationic lipids for gene delivery are preferably used in association with a neutral lipid such as DOPE (dioleyl phosphatidylethanolamine), as described in WO 90/11092 as an example.

Formulation containing cationic liposomes may optionally contain other transfection-facilitating compounds. A number of them are described in WO 93/18759, WO 93/19768, WO 94/25608, and WO 95/02397. They include spermine derivatives useful for facilitating the transport of DNA through the nuclear membrane (see, for example, WO 93/18759) and membrane permeabilizing compounds such as GALA, Gramicidine S, and cationic bile salts (see, for example, WO 93/19768).

Gold or tungsten microparticles may be used for gene delivery, as described in WO 91/00359, WO 93/17706, and Tang et al., (1992). The microparticle-coated polynucleotide is injected via intradermal or intraepidermal routes using a needleless injection device ("gene gun"), such as those described in U.S. Pat. No. 4,945,050, U.S. Pat. No. 5,015,580, and WO 94/24263. Otherwise, naked DNA can be directly injected, i.e. intramuscularly.

The amount of DNA to be used in a vaccine recipient depends, e.g., on the strength of the promoter used in the DNA construct, the immunogenicity of the expressed tumor antigen, the condition of the mammal intended for administration (e.g., weight or age), the mode of administration, and the type of formulation. In general, a therapeutically effective dose from about 1 μg to about 1 mg, preferably, from about 10 μg to about 800 μg and, more preferably, from about 25 μg to about 250 μg, can be administered to human adults. The administration can be achieved in a single dose or repeated at intervals.

The route of administration is any conventional route used in the vaccine field. As general guidance, a nucleic acid of the invention may be administered via a parenteral route, e.g., by an intradermal, intraepidermal, or intramuscular route. The choice of administration route depends on the formulation that is selected. A polynucleotide formulated in association with bupivacaine is advantageously administered into muscles. When a neutral or anionic liposome or a cationic lipid, such as DOTMA or DC-Chol, is used, the formulation can be advantageously injected via intramuscular or intradermal routes. A polynucleotide in a naked form can advantageously be administered via the intramuscular, intradermal, or subcutaneous routes. In addition electroporation can be developed to improve delivery of DNA to muscle (Mir et al., 1999).

The nucleic acid therapy is combined with administration of a non-immunosuppressive inducer of tumor cell apoptosis, such as arsenic, low dose chemotherapy or all-trans retinoic acid or other retinoic acid compounds—as 9-cis RA, 4 HPR, 13 cis RA, CD437 and other differentiation and apoptosis inducers, activation of CD44 by antibodies or hyaluronic acid, hematopoietic growth and differentiation factors.

A patient is administered with this inducer that is either present in the same vaccine composition as the nucleic acid of the invention, or is present in the form of a separate composition. In the latter, the route of administration may be identical or different to the route of administration used for the nucleic acid. For instance, one may deliver the nucleic acid composition through intradermal or intramuscular routes, whereas the inducer is administered orally.

Therapeutic Applications

The nucleic acids, kits and vaccine compositions of the invention are particularly useful for the treatment of tumor conditions, more particularly cancers. In particular, vaccine compositions comprising PML-RARα as the tumor antigen are useful for the treatment of acute promyelocytic leukemia. Examples of antigens useful for cancer therapy include AML1/ETO for the treatment of acute myeloid leukemia (AML) type M2, CBF beta/MYH11 in AML type M4 Eosinophilia, Tel/PDGF for chronic myelomonocytic leukemia (CMML), PLZF-RARα in variant acute promyelocytic leukemia, MLL fusions in various lymphoid or myeloid leukemia, TEL/AML-1 for childhood acute lymphoblastic leukemia and BCR/ABL for the treatment of chronic myelogenous leukemia.

A further subject of the invention is thus a method for treating a tumor condition, which method comprises administering to a patient in need of such treatment a therapeutically active amount of (i) a non-immunosuppressive inducer of tumor cell apoptosis and (ii) a nucleic acid comprising a sequence that encodes an immunogenic polypeptide, and in particular a tumor antigen.

Another subject of the invention is the use of a vaccine composition, a kit, or specific nucleic acids as defined above for the preparation of a medicament useful for the treatment of a tumor condition, e.g. cancers.

The invention will be further understood in view of the following examples and the annexed figures.

FIGURES

FIG. 1 illustrates a representative protocol of a preclinical trial. APL: acute promyelocytic leukemia, ATRA: all-trans retinoic acid, D=day, DNA=injection of DNA.

FIG. 2 represents the DNA vaccination protection against disease progression. 2A: Kaplan Meier survival curves of mice injected with APL cells treated with placebo, with or without the PML-RARαFrC construct. 2B: Kaplan Meier survival curves of mice injected with APL cells treated with ATRA, with or without the PML-RARαFrC construct. 2C: Kaplan Meier survival curves of mice injected with APL cells treated with placebo or ATRA, with the full length pCINPML-RARα construct. Procedural deaths were censored (shown in solid diamond symbols).

FIG. 3 illustrates the cumulative survival and RARα antibody response. The threshold was set at Ua=1. There were n=19 positive and n=28 negative antibody producers. This threshold was determined arbitrarily based on the dilution of the positive control, an anti-RARα mouse monoclonal antibody.

FIG. 4 shows the Western blot analysis confirming the antibody production, using anti-RARα antibody (lane 1), control mice sera (lane 2), day 18 vaccinated mice sera (lane 3) or day 38 vaccinated mice sera (lane 4).

FIG. 5 illustrates the correlation between the increase in CD4+ (FIG. 5A) and CD8+ (FIG. 5B) T-cells induced by PML-RARα sequences and mice outcome (FIG. 5C). The different T-cell populations for individual mice, treated with ATRA or PML-RARαFrC+ATRA, are shown with their corresponding survival curves. Complete responders (CR), defined as those who remain alive after 120 days, are shown in solid lines, partial responders (PR), those who survived beyond 75 days, are shown in broken dashed lines and non-responders (NR), defined as those who died (crosses) between days 40-60, are shown in dashed lines.

FIG. 10 represents immunoblots showing anti-RARα antibody production

Figure 1:
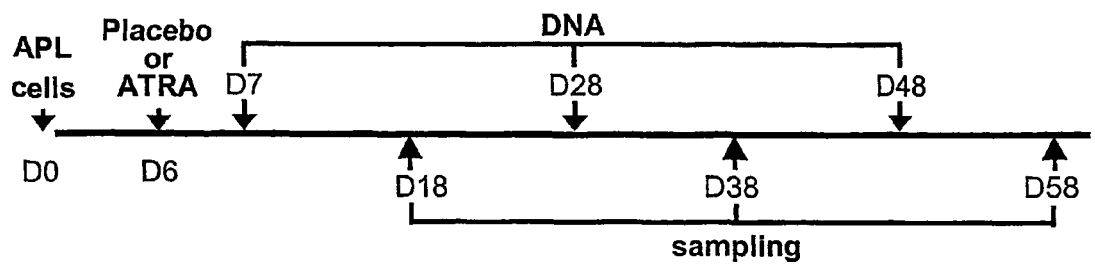

A. Sera from Treated APL Mice Recognize Human and Mouse RARα and the Human Oncogene PML-RARα.

Western blots of protein extracts from: APL mouse spleen cells (lanes 1,2) and healthy mouse spleen cells (lane 3) and were immunoprobed with an anti-RARα antibody monoclonal antibody 9αF (lane 1), a day 58-serum from an ATRA-treated APL-mouse (lane 2), or a day 58-serum from an ATRA-treated and PML-RARαFrC DNA-vaccinated mouse (lane 3). Blots display bands with an apparent molecular weight of 50 kDa and 105 kDa, corresponding to RARα and PML-RARα respectively (lanes 1, 2), while only a 50 kDa band was seen with normal spleen cell extract (lane 3). Reprobing the blot with an anti-α-tubulin antibody shows protein loading. Exposure times were respectively: anti-RARα (lane 1: 30 mins); serum Day 58 (lane 2: 2 mins); serum Day 58 (lane 3: 30 secs)—anti-α-tubulin (lanes 1 and 2: 4 hrs), (lane 3: 5 mins).

B. Sera from Full Length PML-RARα-Treated Mice Recognize PML-RARα

NB4 protein extracts immunoprobed with anti-RARα antibody (lane 1), day 18 serum from a mouse treated with ATRA and PML-RARαFrC DNA-vaccine (lane 2) and day 58 serum from an ATRA-treated+full length PML-RARα DNA-vaccinated mouse (lane 3). Reprobing the blot with an anti-α-tubulin antibody shows protein loading. Exposure times were respectively: anti-RARα (lane 1: 30 min); serum Day 18 (lane 2: 5 mins); serum Day 58 (lane 3: 5 mins)—anti-α-tubulin (lanes 1 to 3: 5 mins).

C. Sera from Treated APL Mice Recognize Recombinant GST-RARα Used in the ELISA.

Western blots were performed with a recombinant GST-RARα protein (lanes 1,3) or a control GST protein (lanes 2,4) as confirmed by probing with an anti-GST antibody (lower panel) and an anti-RARα antibody (middle panel). These blots were immunoprobed by with day 18 (lanes 1,2) and day 38 (lanes 3,4) sera from a mouse treated with ATRA and PML-RARαFrC DNA (upper panel). Blots display The bands with an apparent molecular weight of 85 kDa corresponding to recombinant GST-RARα (85 kDa, upper panel) and revealed with an anti-RARα antibody (lane 3, middle panel) is arrowed, while an additional 50 kDa band was seen in lane 1 probably due corresponding to RARα. and when immuno probed with an anti-RARα monoclonal antibody 9αF (lane 1), Exposure times were respectively: serum Day 18 (lanes 1 and 2: 5 mins); serum Day 38 (lanes 3 and 4: 5 mins); anti-RARα (lanes 1 to 4: 5 min).

EXAMPLES

Example 1

Material and ethods 1.a) Animal Model

Transgenic mice using the human PML-RARα cDNA, cloned from a patient with a PML-RARα bcr 1 breakpoint, was previously constructed in the FVB/N inbred strain of mice as described in Brown, D. et al (1997). This fusion contains a amino acid generated by the fusion of PML with RARα specific for the oncoprotein. A transplant model was established from transgenic lines in which blast cells, isolated from spleens of the transgenic animals, were resuspended in 200 µl of buffered saline and injected into the tail vein of 6-8 week old naive syngeneic mice. Peripheral blood counts were conducted using a Hemavet counter (CDC Technologies, Oxford, Conn.). Histological sections were prepared by fixing tissues in buffered formalin and embedded in paraffin blocks. RNA was extracted from the spleen of the mice by caesium chloride centrifugation as described in Chen et al:, (2000). RT-PCR and real time RT-PCR with the Taqman were conducted to confirm the presence of the PML-RARα transcripts and assess the tumor load as described in Cassinat et al., (2000). This model is reproducible in that 100% of the transplanted mice die of the disease, whereas only 30% of the transgenic animals develop leukemia. The number of cells required to successfully produce leukemia in 100% of Naïve syngeneic mice with a life span of 34 weeks has been titrated to $10^4$ blast cells derived from the leukemia spleen of a transgenic mouse. Treatment with ATRA pellets (5 mg or 10 mg 21-day release pellets from Innovative Research, Sarasota, Fla.), administered subcutaneously behind the neck, will rescue these mice from death, but as with human patients treated with ATRA alone, the mice relapse and die in 6-12 weeks post transplant. Cells from the spleen of two independent founders were used (lines 909 and 935) in different protocols with identical results. All procedures complied with European or national regulations on the use of animals for experimentation.

Transgenic models of myeloid malignancy are transgenic mice which have a disease resembling human late stage myelodysplasia (French American & British [FAB] type refractory anemia with excess blast (RAEB), RAEB in transformation RAEBt and chronic myelomonocytic leukemia (CMML). They are doubly transgenic for mutant NRAS and BCL-2 or CBFβ-MYH11 and BCL-2 or triple transgenic mice with mutant NRAS/CBFβ-MYH11/BCL-2.

1.b) DNA Vaccine Construction and Plasmids

PML-RARαFrC Construct

The directional cloning of 105 bp of sequences around the PML-RARα fusion in association with a peptide signal and tetanus toxin fragment C (FrC) sequences into a pCNA$_3$ based vector, clone YJFrC (King et al., 1998) was performed using a Seamless cloning kit (Stratagene) (called PML-RARαFrC). The primer sequences used are shown as follows:

PMLRAR (SEQ ID no 3)
PMLRAR S:
5'-ACTGCTCTTCCTCCGAGGTCTTCCTGCCCAACAGC-3'

(SEQ ID no 4)
PMLRAR AS:
5'-ACTGCTCTTCCTTTCGAGGGAGGGCTGGGCACTAT-3'

YJFC (SEQ ID no 5)
LeaderAS:
5'-ACTGCTCTTCCGGAGTGGGCCCCCGGGGCCAC-3'

(SEQ ID no 6)
Frag C.S:
5'-ACTGCTCTTCCAAAAACCTTGATTGTTGGGTC-3'

The construct was verified by sequencing (UCSF facility). Expression of the PML-RARα fusion and FrC was confirmed by transient transfection of plasmid DNA into COS cells. Bulk plasmid DNA preparations were purified for vaccination using the caesium chloride procedure as described in Sambrook et al. (1989). The full-length pCINPML-RARα (de Thë, H. et al., 1991) was also used.

PML-RARαAS-FrC Construct

The complementary sequence of the 105 base pairs around the PML-RARα fusion has been cloned in frame to fragment C (PML-RARαAS-FrC).

The primer sequences used are shown as follows:

RARPOL S: corresponds to RAR-PML sens—Flip seamless upstream primer 5'-ACTGCTCTTCCTCCCGAGG-GAGGGCTGGGC-3' (SEQ ID no12)

RARPOL AS corresponds to RAR-PML antisense—Flip seamless downstream primer 5'-ACTGCTCTTC-CTTTGAGGTCTTCCTGCCCA-3' (SEQ ID no13)

LeaderAS and Frag C.S were also used,

Partial PML-RARαAS-FrC sequence is shown in SEQ ID no 10:

ScFvBCL1-FrC Construct also Referred to as BCL1-FrC in the Figures

This construct has been obtained from Stevenson laboratory (Southampton, England) and a partial sequence is shown in SEQ ID no11).

1.c) Pre-Clinical Vaccination Protocol

To determine whether vaccination improves treatment once the disease is established, a series of pre-clinical trials on mice transplanted with either $10^4$, $10^6$ or $10^7$ syngeneic APL cells were undertaken to define the best model to mimic the disease and therapy efficacy. One week after injection with APL cells the animals were randomized into one of four groups: placebo, placebo+DNA, ATRA, ATRA+DNA. DNA resuspended in HBSS was injected the day after placebo or ATRA pellet administration. 2 subsequent courses of injections were given intramuscularly in the quadriceps with 2 injections per mouse each time at 20-day intervals (total of 3001 µg DNA for protocol). Samples for blood counts and sera preparation for antibody analyses were collected 10 days after each course of injection. The representative protocol is depicted in FIG. 1. Mice were followed for active disease by measuring blood counts, immunophenotyping of myeloid populations and survival.

1.d) Analytical Methods

Statistical Analysis

Survival was analysed by the Kaplan Meier method and comparisons between groups were by Wilcoxon and log rank tests. Comparisons between groups of antibody response were by students' t test.

Measurement of Antibody Response.

ELISA

Recombinant human RARα protein (rhRARα) was purified from a GST-RARα construct in pGEX2T plasmid as described in Delva et al. (1999). Antibodies against RARα were detected by an ELISA method as described hereafter. Briefly, purified recombinant human RARα protein (rhRARα) was coated in 96-well plates at 10 µg/ml overnight. After saturation and washing steps, diluted (1/50) mouse sera were added and antibodies were revealed by peroxidase-conjugated goat anti-mouse IgG and IgM (Jackson Immuno Research, PA). TMB substrate (BD Pharmingen, San Diego, Calif.) was added for the peroxidase reaction which was stopped with 1M phosphoric acid. Absorbance was measured at 450 nm with a reference filter at 630 nm using an optical densitometer (Dynatech). Each serum was tested in duplicate and specific absorbance was calculated as the difference between the mean absorbance in wells with rhRARα and the mean absorbance in wells without rhRARα. A positive control consisted of an anti-RARα mouse monoclonal antibody (9αF) diluted from 1/1000 to 1/200000. The specific absorbance obtained for each sample was divided to the specific absorbance of 1/200000 dilution of the positive control in order to normalize the results from all experiments and thus to obtain arbitrary units (UA: $1\ U_{A\ sample\ I} = A_{spe\ sample\ I} / A_{spe\ positive\ control\ 1/200\ 000}$). A mouse serum was considered as positive for the presence of anti-RARα antibodies if UA was higher than 1.

Mice have been monitored for FrC antibody production using methods described previously (Spellerberg et al. 1997; King et al., 1998).

Western Blot Analysis

Western blot analysis was performed as described in Delva et al., (1999); Fenaux et al., (2001) using protein extracts from the NB4 cell line. Membranes were immunoprobed overnight with mice sera (1:50 dilution) or anti-RARα antibody (1:800 dilution of 115 or 1/1000 dilution of 9α). After incubation with an antimouse IgG for immune serume from the mice or anti-rabbit IgG antibody horseradish peroxidase conjugate for the polyclonal antibody 115 (Boehringer-Mannheim, Meylan, Germany), immunoreactive proteins were revealed using ECL chemiluminescence detection kit (Amersham, Les Ulis, France).

CTL Cytotoxicity Assays

CTL assays were undertaken as described in Dresser et al., (1968). Briefly, recipient mice were injected with $10^7$ irradiated (25Gy) spleen cells taken from DNA treated animals on Day 40 in the hind footpads. After 3 days cell suspensions were prepared from draining lymph nodes and cells were cultured in vitro for 4 more days in the absence of any stimulating cells in culture medium containing ConA-stimulated rat spleen cell supernatant as a lymphokine source (50 U IL-2/ml). The culture medium was MEM α-medium (Life technologies, Gaithersburg, Md.) supplemented with 100 U/ml penicillin (Life Technologies), 2 mM glutamine (Life technologies), $5 \times 10^{-5}$-ME (Sigma, St. Louis, Mo.) and 10% heat-inactivated FCS (Life Technologies).

Cellular-mediated Immune Response Studies

Cell-mediated cytotoxicity assays were performed to determine whether DNA treated mice generate a CTL response against APL cells. Mixed lymphocyte cultures were set up co-culturing spleen cells from the DNA treated or untreated BALB/c (allogeneic control) mice with irradiated (25 Gy) APL cells. Cell culture medium consisted of MEM α-medium (Life Technologies, Gaithersbourg, Md.) supplemented with 100 U/ml penicillin (Life Technologies), 100 µg/ml streptomycin (Life Technologies), 2 mM glutamine (Life Technologies), $5 \times 10^{-5}$ M 2-ME (Sigma), and 10% heat-inactivated fetal calf serum Life Technologies). After 6 days, the CTL generated in these primary bulk culture were tested in the $^{51}$Cr-release assay.

$^{51}$Cr-release Assay

Five-thousand $^{51}$Cr-labeled target cells (APL or cells from untreated mice stimulated for 48 h with 5 µg/ml Concanavalin A) were incubated with effector cells at various E:T ratios in round-bottom wells for 4 hours. The percentage of specific $^{51}$Cr release was calculated as (experimental−spontaneous release)/(maximum−spontaneous release)×100.

NK Assays

NK activity was evaluated by $^{51}$Cr-release assay using YAC cell lines as target cells as described (Lust et al., 1981).

Proliferation Assay

Long term survivors (post day 300 illustrated in FIG. 2B) were sacrificed and tested for proliferation and cytokine release. Briefly, $5 \times 10^5$ responders (spleen cells from FVB/N injected with APL cells and treated with ATRA+PML-RARα-FrC or ScFvBCL1-FrC) were plated in each well with 200 µl of media consisting of RPMI 1640, 10% FCS and 0.5% 2β-mercaptoethanol. Spleen cells from healthy mice treated with ATRA. Stimulators (spleen cells from FVB/N, APL or BALB/c) were irradiated with 25 Gy and $1 \times 10^6$ cells were added to each well. After 24, 48 and 72 hours of incubation cells were assayed for $^3$H-thymidine incorporation and supernatants were harvested for cytokine release assays. Cultures were set up in duplicate.

Cytokine Release Assay

Figure 8:
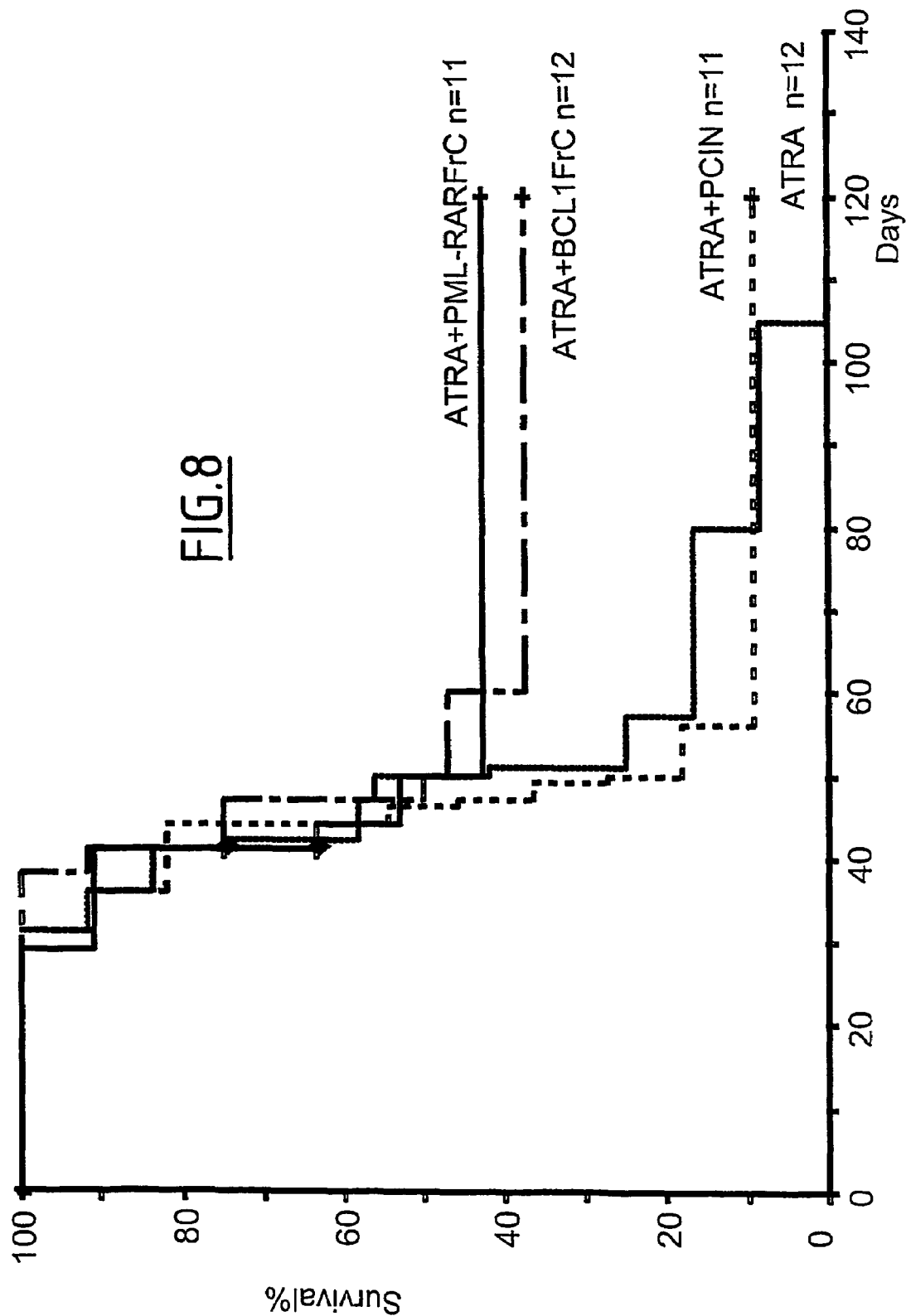
FIG. 8 represents the DNA vaccination protection against disease relapse. Kaplan Meier survival curves of mice injected with APL cells treated with ATRA alone, ATRA with empty vector pCIN, ATRA with ScFvBcl1FrC construct, ATRA with PML-RARαFrC construct.
Figure 9:
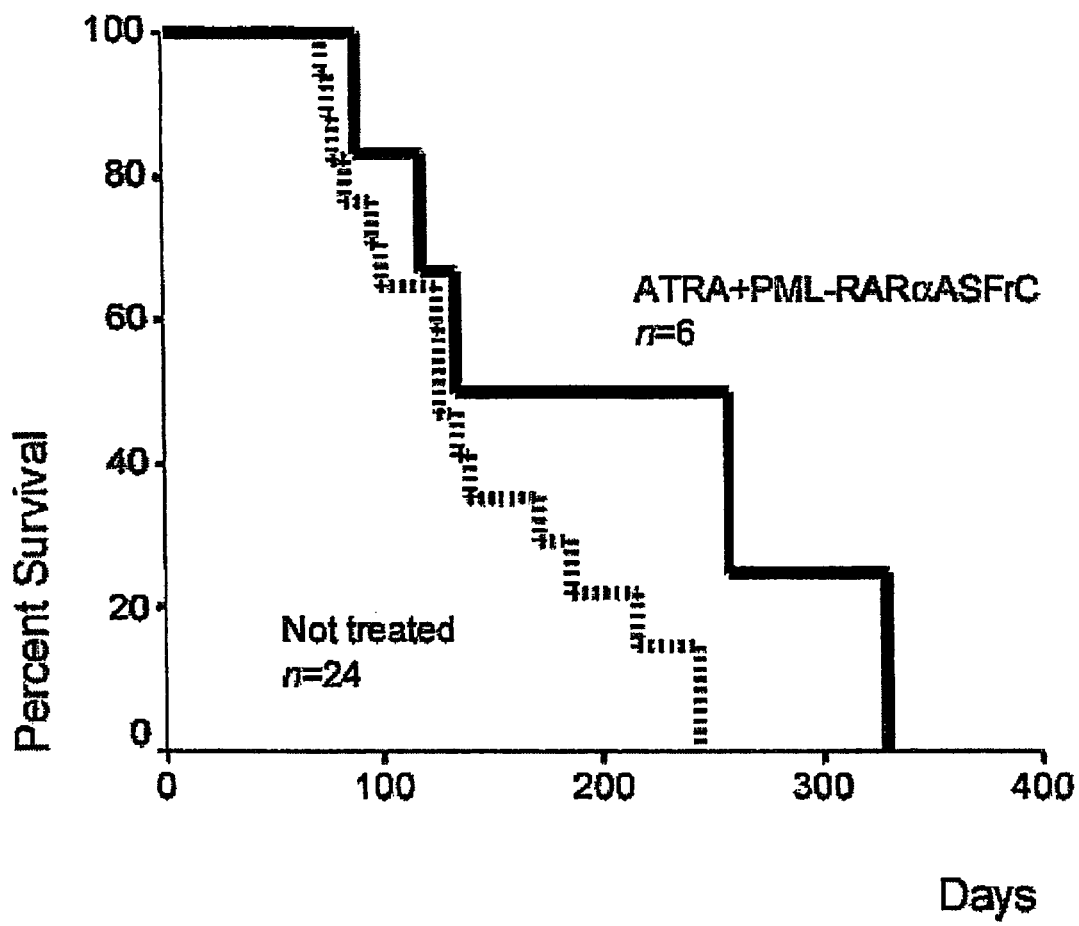
FIG. 9 represents the efficacy of the vaccine composition comprising ATRA (10 mg daily release for 21 days) and PML-RARαAS-FrC construct in transgenic models of myeloid malignancy.
Figure 9:
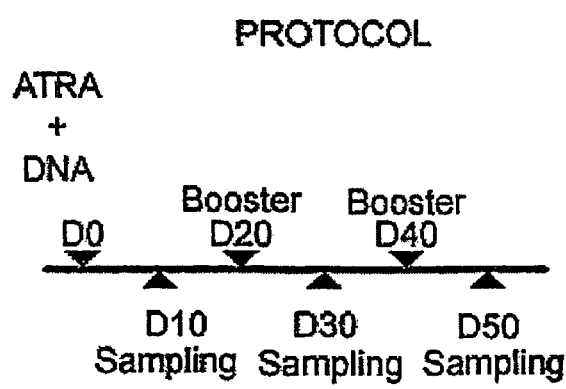

Cytokine release was measured using a mouse Th1/Th2 cytokine cytometric bead array kit according to the manufacturers protocols (Becton, Dickinson, Pharmingen, San Jose, Calif.). This kit measures cytokines IL-2, IL4, IL-5, IFN-γ and TNF-α. Long-term survivors of the mice from the protocol illustrated in FIG. 8, were sacrificed and spleen cells were cultured as described above. Briefly, 50 µl of supernatant was incubated with 50 µl of the mixed capture beads and 50 µl of the mouse Th1/Th2 PE detection reagent for 2 hours and analyzed on a FACSCalibur cytometer. Analysis was undertaken using the BD CBA (Becton Dickinson, Pharmingen) and Cell Quest software.

Flow Cytometric Analysis

T-cell and NK expression was measured from peripheral blood using cell surface markers CD4, CD8 and CD3 with FITC or PE conjugated antibodies that were purchased from Becton Dickinson/Pharmingen (San Jose, Calif.). Cells were stained according to protocols provided by manufacturers and analyzed a FACSCalibur cytometer. Flow cytometric analyses were performed at 10 day intervals after DNA injection in the pre-clinical protocol Analysis was undertaken using the Cell Quest software (Becton-Dickinson, San Jose, Calif.).

Example 2

Results 2.a) Animal Model of Acute Promyelocytic Leukemia I

The designed pre-clinical trial consisted in first transplanting cells from APL transgenic mice in syngeneic mice to establish disease. Once leukemia was established, mice were separated in two therapeutic arms (placebo versus ATRA) and subsequently assigned to either PML-RARα FrC DNA or various plasmid controls (FIG. 1 and summarised in Table 1). Three injections at 20 day intervals were performed. The injected PML-RARα FrC DNA consisted of a 105 bp sequence around the fusion of PML-RARα cloned downstream of the CMV promoter and leader sequences and in frame with fragment C sequences from tetanus toxin, PML-RARα FrC.

TABLE 1

Summary of survival of mice on the pre-clinical trial

|  | No. mice/total (survivors %) | | |
|---|---|---|---|
|  | Day 30 | Day 60 | Day 120 |
| Placebo | 0/12 (0%) | 0/12 (0%) | 0/12 (0%) |
| Placebo + pCINPML-RARα | 0/12 (0%) | 0/12 (0%) | 0/12 (0%) |
| Placebo + PML-RARαFrC | 6/11 (56%) | 2/11 (18%) | 0/11 (0%) |
| ATRA | 24/24 (100%) | 5/24 (21%) | 0/24 (0%) |
| ATRA + pCINPML-RARα | 12/12 (100%) | 4/12 (33%) | 0/12 (0%) |
| ATRA + PML-RARαFrC | 23/23 (100%) | 11/23 (48%) | 10/23 (44%) |

Monitoring of peripheral blood counts showed that placebo treated mice developed high leukocyte and low platelet counts, which confirmed the established disease as previously described in Dresser et al., (1968). Post mortem autopsies showed that in all cases the organs were enlarged. Examination of tissue sections showed invasion around the periportal cavities of liver and spleens with acute promyelocytic blast cells confirming that cause of death was due to APL. RNA extracted from the spleen cells at different time points in some mice further confirmed by RT-PCR the presence of the PML-RARα transcript.

Figure 2A:
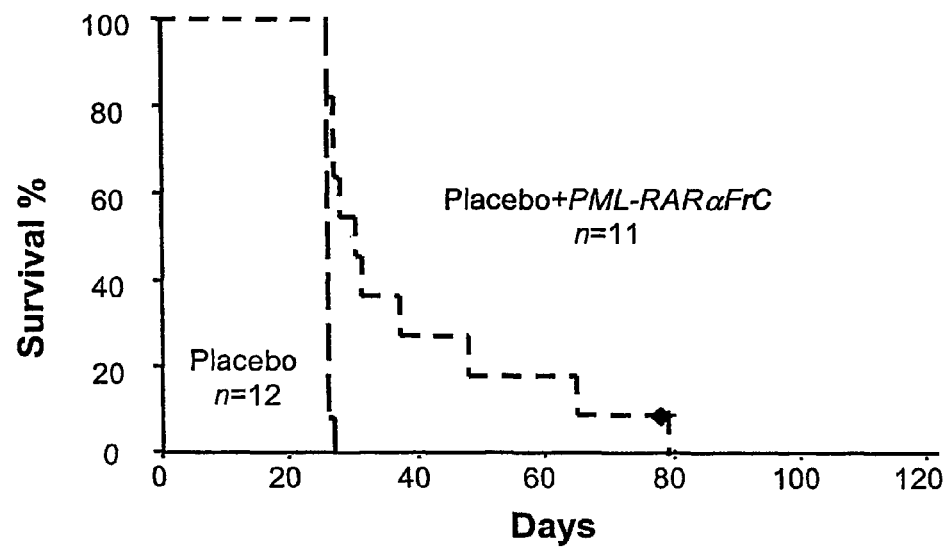
Figure 2B:
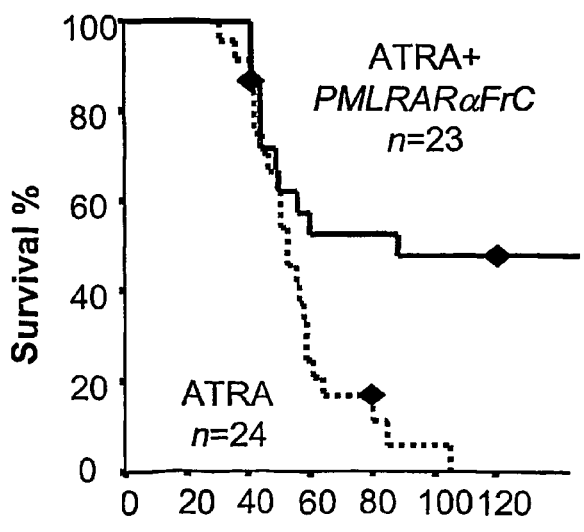
Figure 2C:
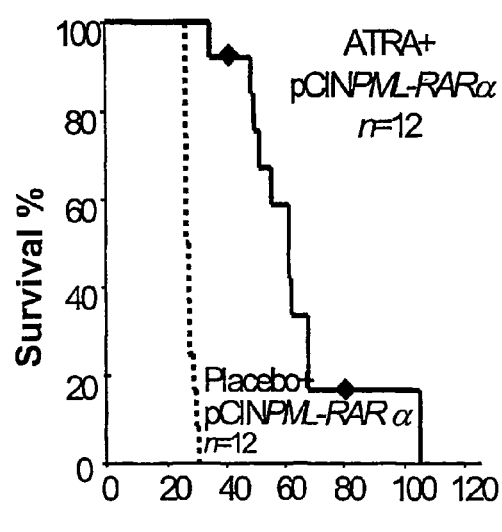

2.b) The combination of DNA PML-RARαFrC and ATRA Dramatically Increases the Survival of Treated Mice Survival analyses show that mice without ATRA (placebo arm) had significantly extended survival when treated with PML-RARαFrC compared to mice with placebo alone. (FIG. 2A, p<0.001). Likewise, in ATRA-treated mice, addition of PML-RARαFrC prolonged survival by extending survival in 50% of the animals (p<0.02). Compared to mice treated with PML-RARαFrC alone, ATRA+PML-RARαFrC treated mice had a significant enhanced survival (p<0.002). Overall statistical analysis of the different therapeutic arms, (placebo, ATRA alone or ATRA+PML-RARαFrC), confirms the advantage of the combination therapy (ATRA+DNA vaccination, p=<0.0001). Further protocols conducted at different times confirm these results and provide several criteria for DNA vaccination efficacy in this APL transplantable model. The ATRA alone (n=24) and the ATRA+PML-RARαFrC (n=23) treated mice differ significantly (p<0.01). Furthermore, as most of the long term survival occurred in the latter part of the curve, the statistical analysis was repeated for two periods pre and post day 50 and the differences between these arms post day 50 were highly significant (p<0.001, logrank). The first criterion for DNA vaccination efficacy is tumor burden; indeed mice models created with the injection of more than $10^6$ APL cells did not give statistically significant differences. The second criterion related to the type of plasmid construct injected (FIG. 1 and Table 1). It was clearly apparent that the addition of Fragment C was crucial for enhanced survival, (from 48% survival with the PML-RARαFrC versus 33% with the full length PML-RARα constructs at day 60 in the ATRA arms), with the latter construct showing no significant differences from the control placebo and ATRA arms respectively. At day 120, 44% of the mice in the former arm remain alive compared to none in the latter (Table 1).

Figure 3:
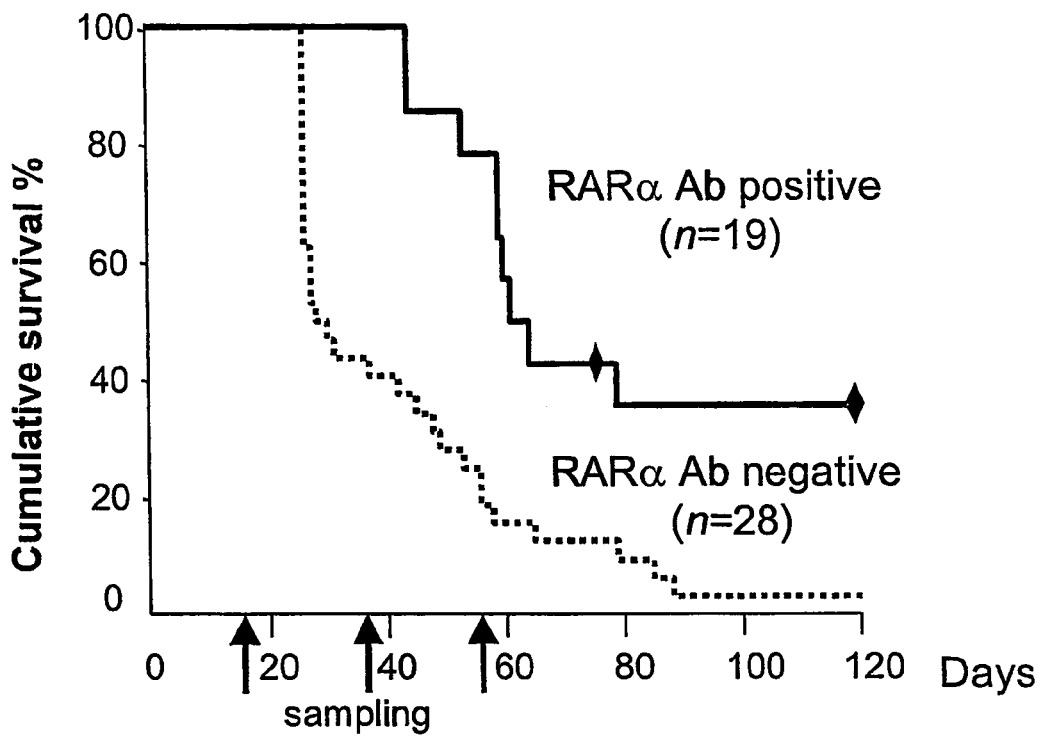
Figure 4:
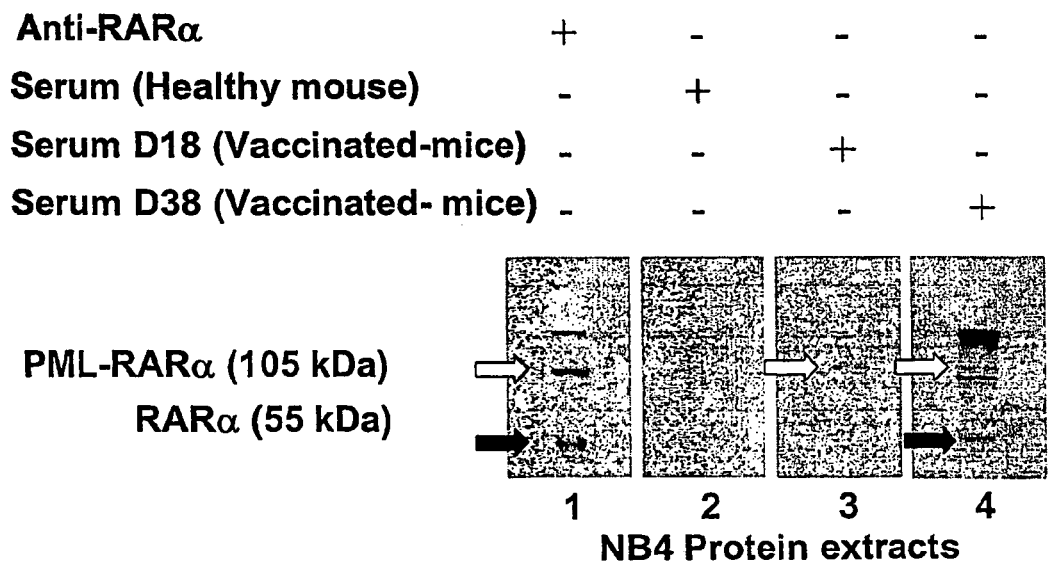
Figure 5C:
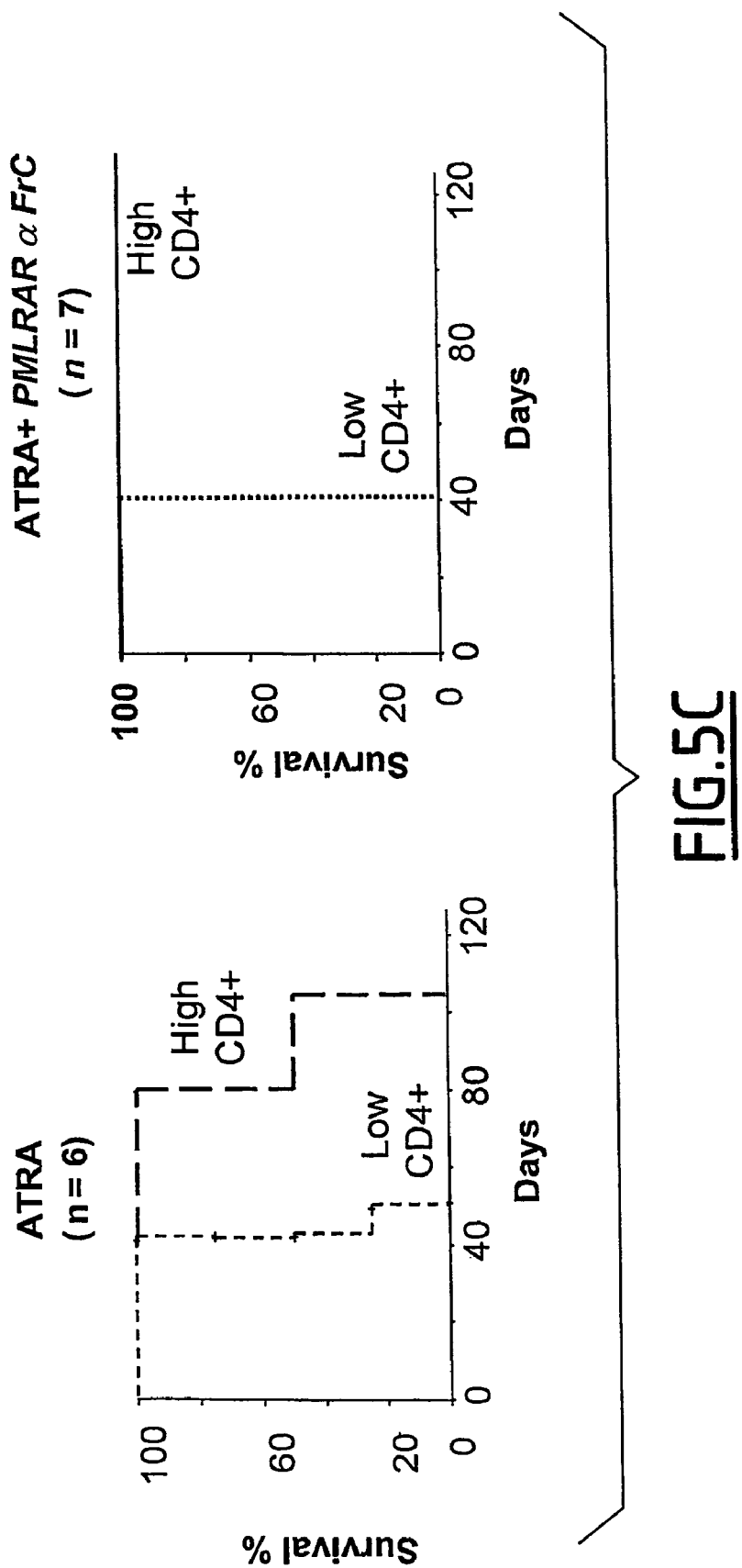
Figure 6:
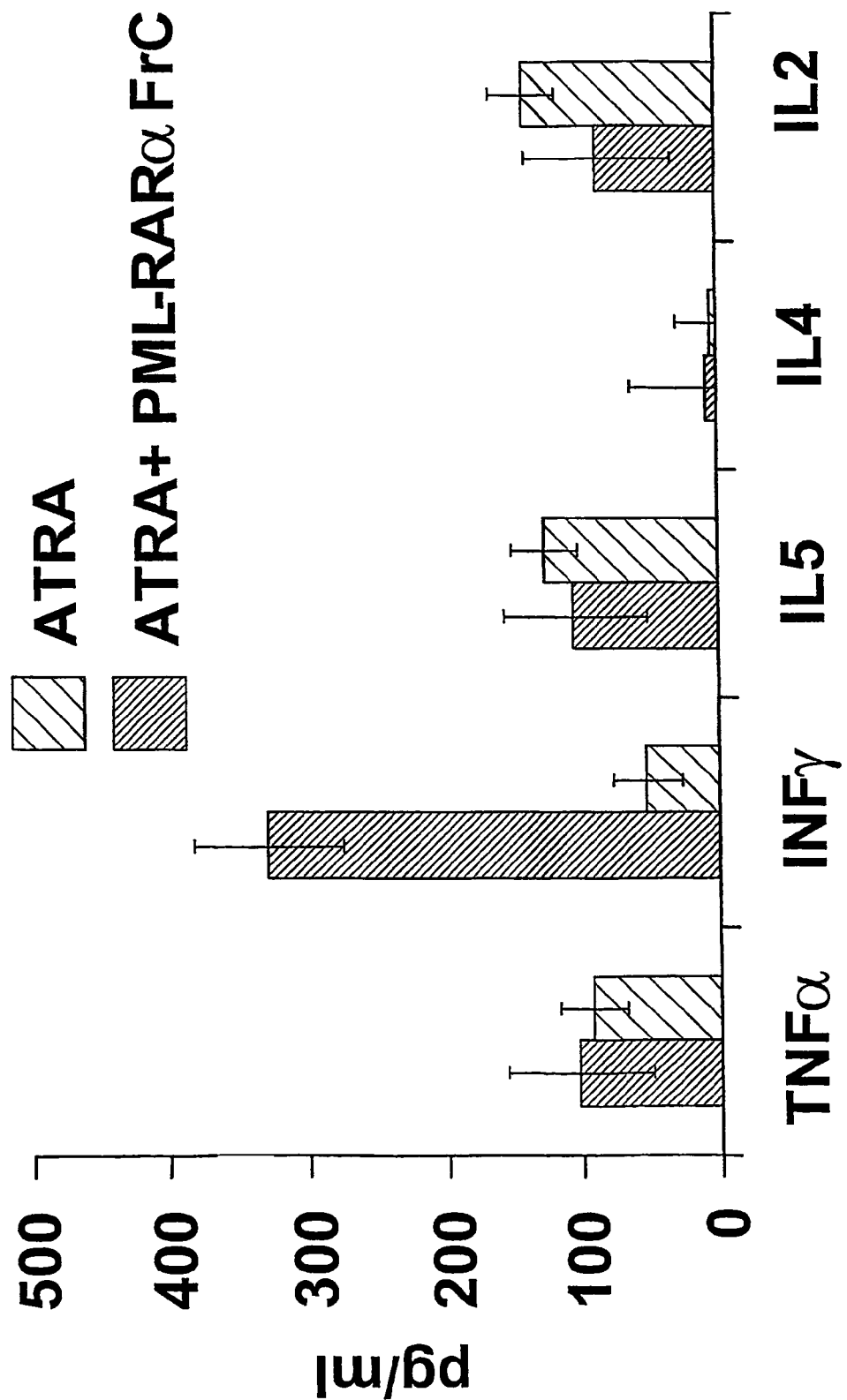
FIG. 6 represents an histogram showing increase in IFN-γ in APL mice after treatment with ATRA+PML-RARαFrC compared with healthy FVB/N mice treated with ATRA. The mean values±S.E. (n=3) obtained after stimulation with irradiated APL cells.
Figure 7:
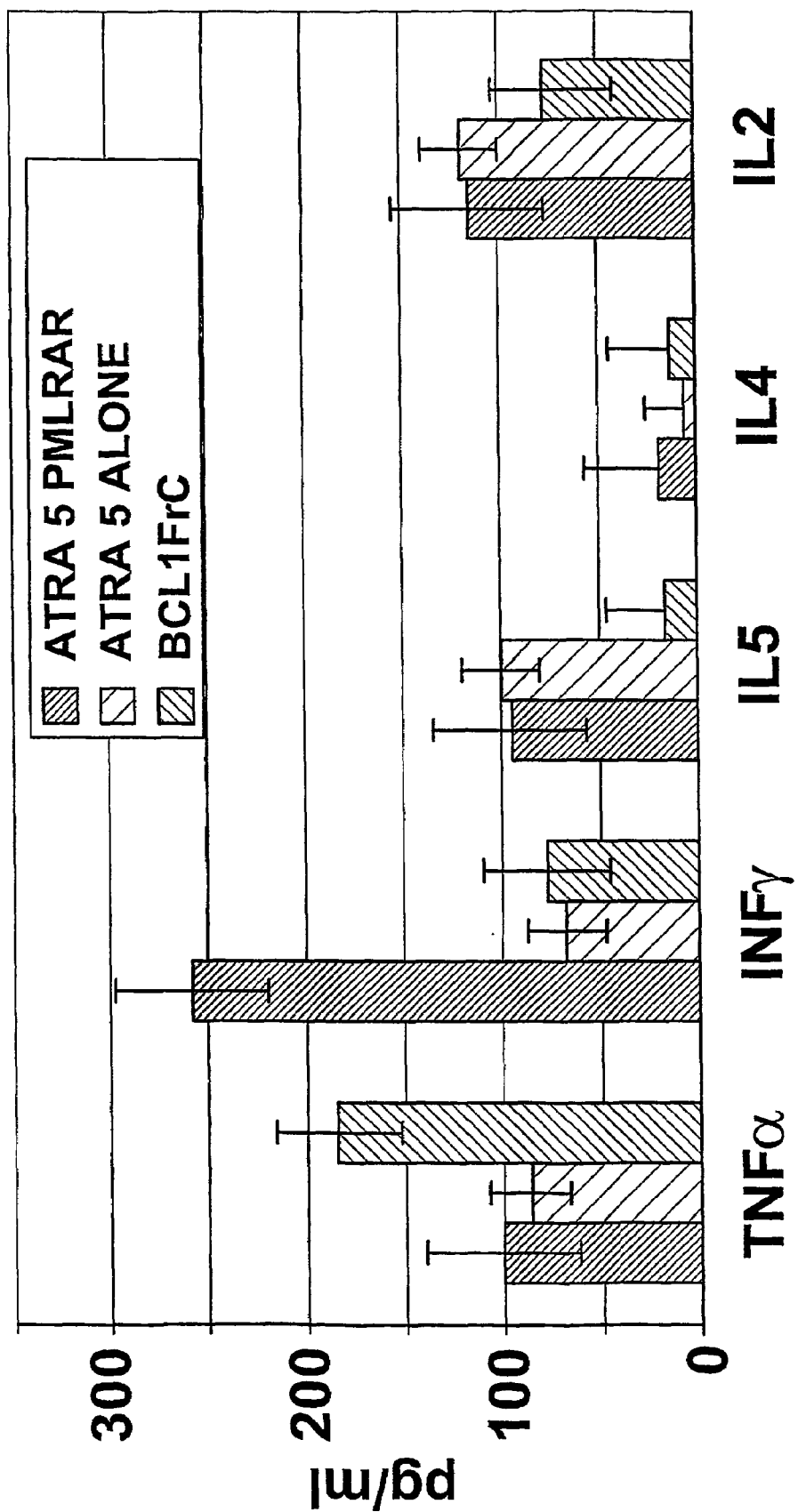
FIG. 7 represents an histogram showing cytokine (TNFα, IFNα, IL5, IL4, IL2) release after 48 hours of culture with irradiated APL cells as stimulators associated with FVB/N mice treated with ATRA 5 mg (daily release for 21 days) alone, APL mice treated with ATRA 5 mg+PML-RARαFrC, or ScFvBcl1FrC (referred asBcl1FrC in figures).

2.c) A Specific Antibody Response Against RARα is Elicited by PML-RARαFrC Vaccination and Further Increased with ATRA In order to assess the mechanisms responsible for the enhanced response to the DNA vaccine protocol, we monitored mice for antibody production and cell-mediated immune response. An ELISA technique was set up to detect RARα antibodies in the serum of mice at different time intervals. Significant levels of antibodies against RARα were detected in ATRA-treated mice with or without DNA vaccine but not in mice with placebo or DNA vaccine alone (Table 2). Although this was true for both ATRA treated arms, the level of antibody produced appeared higher with ATRA alone. However, the difference between the ATRA arms was not significant. Interestingly, in a retrospective analysis, mice which had produced antibody at least once had a survival advantage (FIG. 3, P<0.001). We confirmed the specificity of the ELISA test by Western blot analysis (FIG. 10B). When the serum drawn at day 18 and day 38 of a mouse treated with ATRA+PML-RARαFrC DNA was applied to a nitrocellulose filter with proteins extracted from the PML-RARa[+] NB4 cell line, it detected at least two bands, one with a molecular mass of 105 kDa (lanes 2 and 3) and one of 50 kDa (lane 3). Compared to the same filter immunoblotted with an anti-RARα antibody (lane 1), these two bands correspond in size to PML-RARα and RARα respectively.

TABLE 2

RARα antibody production in mice increases with duration of treatment

|  |  | Day 18 | Day 38 | Day 58 |
|---|---|---|---|---|
| Placebo | Ab positive[1] (%) | 0/12 | 0/12 | 0/12 |
|  | m ± SD[2] | NA | NA | NA |
|  | Median[2] | NA | NA | NA |
| Placebo + PML-RARαFrC | Ab positive[1] (%) | 0/11 | 0/11 | 0/11 |
|  | m ± SD[2] | NA | NA | NA |
|  | Median[2] | NA | NA | NA |
| ATRA | Ab positive[1] (%) | 0/12 | 7/12 (58%) | 4/5 (80%) |
|  | m ± SD[2] | NA | 2.22 ± 1.18 | 13.03 ± 5.41 |
|  | Median[2] | NA | 1.95 | 15.09 |
| ATRA + PML-RARαFrC | Ab positive[1] (%) | 1/12 (8%) | 5/12 (42%) | 7/7 (100%) |
|  | m ± SD[2] | 1.79 | 2.35 ± 1.71 | 3.78 ± 3.9 |
|  | Median[2] | NA | 1.82 | 2.44 |

NA = Not applicable
[1]Number of mice presenting with detectable antibodies/number of mice alive at that date
[2]Values are given as mean, standard deviation (S.D.) and median of Ua from Antibody positive mice.

2.d) A Specific Antibody Response Against FrC is Elicited by PML-RARαFrC+ATRA Vaccination Mice have been monitored for FrC antibody production using methods described previously (Spellerberg et al. 1997; King et al., 1998). In the vaccine protocol, mice treated with 5 mg ATRA/day for 21 days did not make antibodies to fragment C. An increase of dose to 10 mg ATRA/day for 21 days elicited an antibody response to fragment C in 2/2 mice tested whereas no antibodies to fragment C was detected in the single mouse treated with 10 mg ATRA alone without DNA.

In this case it is the combination of DNA and ATRA alone, which induces the antibody response as fragment C is not expressed by the mouse cells normally. Part of the explanation of the mechanism is that the cells which take up the exogenous DNA and process the protein (in vivo transfection) are induced to apoptose by ATRA and the fragment C antigen is taken up by antigen presenting cells (APCs) to induce antibody production in this way.

2.e) Mice Treated with PML-RAR$\alpha$FrC+ATRA have Increased Level of CD4+ or CD8+ Cells An increase in CD4+ and CD8+ cells from peripheral blood was observed at day 18 in mice who had partial or complete responses, which were predominantly those treated with ATRA+PML-RAR$\alpha$FrC (FIGS. 5A and 5B).

The NK population was increased in APL mice compared to the FVB/N control mice and in the mice injected with pCINPML-RAR$\alpha$ and with the mice injected with PML-RAR$\alpha$-FrC. No difference in NK activity was detected in the spleens from any immunized animals compared to normal FVB/N controls. Although we were able to confirm in an allogeneic setting, that CTLs could be generated in these FVB/N mice, we were unable to detect significantly elevated cytotoxic T cells (CTLs). This could be explained either by the usually low quantity of CTLs produced and/or the lack of competent target cells in this model.

The survival data show that the PML-RAR$\alpha$-FrC construct confers extended life span either alone or in combination with ATRA and that fragment C sequences are necessary for increased survival. The significant extended life span after vaccination suggests that anti-APL responses have been induced by the DNA vaccine route confirmed by the increase in CD4+ cells and the increase of anti-RAR$\alpha$ antibodies. As it was previously referred as that irradiated APL cells alone could elicit an antibody response, this immune effect is likely to be specific, triggered by the APL cells as a source of tumor antigen. Indeed, the ELISA assays showed an antibody response specifically against RAR$\alpha$ in ATRA treated mice. This antibody production can be correlated to the increase in CD4+ T cells which are known to be effectors of DNA vaccine using this FrC construct (King et al., 1998; Bogen et al., 1996; Rice et al., 2001). Other DNA or peptide vaccine mouse models have reported similar results of antibody production (King et al., 1998; Spellerberg et al., 1997). CD4+ T cells are implicated in establishing immune memory and may explain the prolonged or retarded effect (Chen et al., 2000).

2.f) Mice Treated with PML-RAR$\alpha$FrC+ATRA have Increased Level of Interferon-Gamma Proliferation and cytokine release assays were conducted on long-term survivors, (i.e. mice treated with either ATRA alone or ATRA and PML-RAR$\alpha$FrC from the trial shown in FIG. 2B). Though spleen cells from ATRA and PML-RAR$\alpha$FrC mice could be induced to proliferate in the presence of allogeneic Balb/c spleen cells, they did not proliferate more than control FVB/N spleen cells when stimulated with syngeneic APL cells (data not shown).

In contrast, a specific increase in INF-$\gamma$ (6-fold) after 48 hours of culture was noted when spleen cells from mice treated with the ATRA and PML-RAR$\alpha$FrC combination were stimulated with irradiated APL cells compared with spleen cells from healthy mice treated with ATRA alone (327 pg/ml versus 52 pg/ml) ($P<0.02$) (FIG. 6). No significant differences were observed for other cytokines such as IL-2, IL-4, IL-5 and TNF$\alpha$. All of these cytokines increased when the same effector spleen cells were co-cultured with Balb/c spleen cells.

2.g) Mice Treated with ScFvBCL1-FrC+ATRA or PML-RAR$\alpha$ASFrC+ATRA have Increased Lifespan and Increased Level of TNF$\alpha$.

When using an irrelevant (i.e non specific) construct such as ScFvBCL1-FrC (FIG. 8) or PML-RAR$\alpha$AS-FrC (FIG. 9), it has been observed that mice had extended lifespan with increases in TNF$\alpha$ approximately one year from injection of APL cells.

In particular, the combination of ATRA+PML-RAR$\alpha$ASFrC was effective at extending the lifespan of transgenic mice RAS/BCL-2 or CBF$\beta$-MYH 1/BCL-2 or RAS/CBF$\beta$-MYH11/BCL-2 who would usually die of a late myelodysplastic syndrome type of disease (of bone marrow failure) (FIG. 9).

Antisense sequences are highly immunogenic as they do not normally exist and are therefore "foreign" to the body. Accordingly, they cause no danger of autoimmunity.

The DNA in this setting is acting as an adjuvant. This combination should work against other cancers as the apoptotic properties of the retinoid to induce the tumour cells to apoptose are exploited to shed tumour associated antigens and the combined effect of retinoids to induce Th2 and antibody and DNA to induce Th1 and CTLs for long term therapeutic effect.

In the experiment reported above, the longest-lived mouse went out to about one year and then succumbed to disease. However, it has to be recalled that unlike the transplant model, where potentially a cure is possible, in a transgenic model, the abnormal gene will always win as these cells cannot be eradicated as they are in the germ line. However, most cancers are somatically acquired and few are hereditary.

As conventional ATRA-based APL therapy regimens are already very good in inducing complete remissions and prolonged survival in human APL, DNA vaccination in this context may have its additional benefit in the control of minimal residual disease, where leukemia cells may be less sensitive to previously administered drugs. This is also the time where vaccination may prove most effective as the inventors have shown that the immune response and efficacy of the DNA vaccination is correlated with the tumor burden.

More generally, the present results show that DNA vaccination should be combined with ATRA. The adjuvanticity of vitamin A has been well described (Dresser et al., 1968), but the present study further stresses that its active metabolite, ATRA, is a good adjuvant for boosting immune response of DNA expression.

ATRA, in addition to its properties of inducing Th2 responses, induced differentiation. The subsequent apoptosis and antigen shedding allowed immune responses of antibody production as measured by ELISA using recombinant RARA. This accounted for the observation for the first time that APL mice treated with ATRA alone made anti-RAR$\alpha$ antibodies, which correlated with improved survival (see above). However as with human APL, ATRA alone was not sufficient and all of the mice relapse and die. The fragment C constructs appear to be necessary to synergise with ATRA to rescue the mice from leukaemia induced death. In contrast to the mice treated with the specific construct ATRA+PML-RAR$\alpha$FrC where IFN$\gamma$ is increased (see above), TNF$\alpha$ is increased in mice who responded to the treatment of ATRA+ScFcBCL1FrcDNA (FIG. 7).

The DNA induced Th1 responses are hypothesized to lead one to CTL and NK activity as potential mechanisms of protection. Both TNF$\alpha$ and IFN$\gamma$ are secreted in Th1 responses by activated T cells, however, it is interesting to note that with the specific construct IFNγ is increased, whereas with the non-specific construct, TNFα is used.

The hypothesis is thus that ATRA induces apoptosis and also promotes antibody responses, whilst the DNA elicits a Th1 response resulting in either CTLs or NK mediated immune surveillance of the malignant cells.

In summary, the pre-clinical data reported in this study show that the PML-RARαFrC construct confers extended life span either alone or in combination with ATRA. Furthermore, this study shows for the first time that the adjuvanticity of the combination of ATRA and fragment C may help maintain clinical remissions by boosting immune responses against tumor antigens generated by diseased individuals.

REFERENCES

Bogen et al., (1996) *Eur J Immunol* 26, 2671-9.
Brown et al., (1997) *Proceedings of the National Academy of Sciences of the United States of America* 94, 2551-6.
Cassinat, B. et al. (2000) *Leukemia* 14, 324-328.
Chen, S. A. et al. (2000) *Clin Cancer Res* 6, 4381-8.
de Thé, H. et al. (1991) *Cell* 66, 675-84.
Delva et al. (1999) *Molecular & Cellular Biology*, 19, 7158-67.
Dengler et al. (1995) *Anticancer Drugs*. 6, 522-32.
Dermime, S. et al. (1996) *Clinical Cancer Research* 2, 593-600.
Dresser, D. W. (1968) *Nature* 217, 527-9.
Fairweather and Lyness (1986) *Nuc. Acid Res.* 14, 7809-7812.
Fairweather et al. (1986) *J. Bacteriol.* 165, 21-27.
Fenaux et al. (2001) *Seminars in Hematology* 38, 13-25.
Gambacorti-Passerini, C. et al. (1993) *Blood* 81, 1369-75.
Gorczyca, (1993) *Cancer Res* 53, 1945-51.
King, C. A. et al. (1998) *Nature Medicine* 4, 1281-6.
Lallemand-breitenbach et al. (1999) *J Exp Med* 189, 1043-1052.
Lust et al., (1981) *Journal of Experimental Medicine* 154, 306-17.
Mir et al., (1999) Proc Natl Acad Sci USA 96, 4262-4267.
Raff, M. (1998) Nature. 396, 119-122.
Rice et al., (2001) *J Immunol* 167, 1558-65.
Sambrook, (1989) *Molecular Cloning. A Laboratory Manual*, (Cold Spring Harbor Laboratory Press, New York.
Spellerberg et al., (1997) *Journal of Immunology* 159, 1885-92.
Stevenson, F. K. et al. (1995) *Immunological Reviews* 145, 211-28.
Syrengelas et al., (1996) *Nature Medicine* 2, 103841.
Tang et al. Nature (1992) 356, 152.
Yun et al., (1999) *Tissue Antigens* 54, 153-61.

The invention claimed is:

1. A vaccine composition comprising (i) a non-immunosuppressive inducer of tumor cell apoptosis and (ii) a nucleic acid comprising a sequence encoding PML-RARα, wherein the non-immunosuppressive inducer of tumor cell apoptosis is selected from the group consisting of arsenic, all-trans retinoic acid, 9-cis RA, 4 HPPR and 13 cis RA.

2. The vaccine composition according to claim 1, wherein the nucleic acid further comprises a sequence that encodes a polypeptide selected from the group consisting of tetanus toxin fragment C (FrC), cholera toxin (CT), *E. Coli* heat-labile toxin (LT), *Clostridium difficile* toxin A and pertussis toxin (PT).

3. The vaccine composition according to claim 2, wherein the polypeptide comprises a tetanus toxin fragment C (FrC).

4. The vaccine composition according to claim 2, wherein the sequence encoding PML-RARα and the sequence that encodes a polypeptide are fused in frame.

5. A method of treatment of cancer comprising administering a composition according to claim 1 to a patient in need of treatment therefrom, wherein said patient exhibits an extended life span as compared to a patient not so treated.

6. The method of claim 5, wherein the cancer is acute promyelocytic leukemia.

7. The vaccine composition of claim 1, wherein the PML-RARα has a sequence selected from the group consisting of SEQ ID NOs: 1, 2 and 7.

* * * * *

```
                           SEQUENCE LISTING

<160> NUMBER OF SEQ ID NOS: 13

<210> SEQ ID NO 1
<211> LENGTH: 105
<212> TYPE: DNA
<213> ORGANISM: Artificial
<220> FEATURE:
<221> NAME/KEY: misc_feature
<223> OTHER INFORMATION: PML-RAR alpha

<400> SEQUENCE: 1
gaggtcttcc tgcccaacag caaccacgtg gccagtggcg ccggggaggc agccattgag     60
acccagagca gcagttctga agagatagtg cccagccctc cctcg                   105

<210> SEQ ID NO 2
<211> LENGTH: 1461
<212> TYPE: DNA
<213> ORGANISM: Artificial
<220> FEATURE:
<221> NAME/KEY: misc_feature
<223> OTHER INFORMATION: PML-RAR alpha-FrC

<400> SEQUENCE: 2
gaggtcttcc tgcccaacag caaccacgtg gccagtggcg ccggggaggc agccattgag     60
acccagagca gcagttctga agagatagtg cccagccctc cctcgaaaaa ccttgattgt    120
tgggtcgaca acgaagaaga catcgatgtt atcctgaaaa agtctaccat tctgaacttg    180
gacatcaaca acgatattat ctccgacatc tctggtttca actcctctgt tatcacatat    240
ccagatgctc aattggtgcc gggcatcaac ggcaaagcta tccacctggt taacaacgaa    300
tcttctgaag ttatcgtgca caaggccatg gacatcgaat acaacgacat gttcaacaac    360
ttcaccgtta gcttctggct gcgcgttccg aaagtttctg cttccacct ggaacagtac    420
```

```
ggcactaacg agtactccat catcagctct atgaagaaac actccctgtc catcggctct    480
ggttggtctg tttccctgaa gggtaacaac ctgatctgga ctctgaaaga ctccgcgggc    540
gaagttcgtc agatcacttt ccgcgacctg ccggacaagt caacgcgta cctggctaac    600 aaatgggttt tcatcactat cactaacgat cgtctgtctt ctgctaacct gtacatcaac    660
ggcgttctga tgggctccgc tgaaatcact ggtctgggcg ctatccgtga ggacaacaac    720
atcactctta agctggaccg ttgcaacaac aacaaccagt acgtatccat cgacaagttc    780
cgtatcttct gcaaagcact gaacccgaaa gagatcgaaa actgtatac cagctacctg    840 tctatcacct tcctgcgtga cttctggggt aacccgctgc gttacgacac cgaatattac    900
ctgatcccgg tagcttctag ctctaaagac gttcagctga aaacatcac tgactacatg    960 tacctgacca acgcgccgtc ctacactaac ggtaaactga acatctacta ccgacgtctg   1020
tacaacggcc tgaaattcat catcaaacgc tacactccga caacgaaat cgattctttc   1080 gttaaatctg gtgacttcat caaactgtac gtttcttaca acaacaacga acacatcgtt   1140
ggttacccga agacggtaa cgcttttcaac aacctggaca gaattctgcg tgttggttac   1200
aacgctccgg gtatcccgct gtacaaaaaa atggaagctg ttaaactgcg tgacctgaaa   1260
acctactctg ttcagctgaa actgtacgac gacaaaaacg cttctctggg tctggttggt   1320
acccacaacg gtcagatcgg taacgacccg aaccgtgaca tcctgatcgc ttctaactgg   1380
tacttcaacc acctgaaaga caaaatcctg ggttgcgact ggtacttcgt tccgaccgat   1440
gaaggttgga ccaacgacta g                                            1461

<210> SEQ ID NO 3
<211> LENGTH: 35
<212> TYPE: DNA
<213> ORGANISM: Artificial
<220> FEATURE:
<221> NAME/KEY: misc_feature
<223> OTHER INFORMATION: primer

<400> SEQUENCE: 3
actgctcttc ctccgaggtc ttcctgccca acagc                              35

<210> SEQ ID NO 4
<211> LENGTH: 35
<212> TYPE: DNA
<213> ORGANISM: Artificial
<220> FEATURE:
<221> NAME/KEY: misc_feature
<223> OTHER INFORMATION: primer

<400> SEQUENCE: 4
actgctcttc ctttcgaggg agggctgggc actat                              35

<210> SEQ ID NO 5
<211> LENGTH: 32
<212> TYPE: DNA
<213> ORGANISM: Artificial
<220> FEATURE:
<221> NAME/KEY: misc_feature
<223> OTHER INFORMATION: primer

<400> SEQUENCE: 5
actgctcttc cggagtgggc ccccggggcc ac                                 32

<210> SEQ ID NO 6
<211> LENGTH: 32
```

```
<212> TYPE: DNA
<213> ORGANISM: Artificial
<220> FEATURE:
<221> NAME/KEY: misc_feature
<223> OTHER INFORMATION: primer

<400> SEQUENCE: 6
actgctcttc caaaaacctt gattgttggg tc                                    32

<210> SEQ ID NO 7
<211> LENGTH: 666
<212> TYPE: DNA
<213> ORGANISM: Artificial
<220> FEATURE:
<221> NAME/KEY: misc_feature
<222> LOCATION: (1)..(57)
<223> OTHER INFORMATION: leader VH1
<220> FEATURE:
<221> NAME/KEY: misc_feature
<222> LOCATION: (58)..(109)
<223> OTHER INFORMATION: PML
<220> FEATURE:
<221> NAME/KEY: misc_feature
<222> LOCATION: (111)..(162)
<223> OTHER INFORMATION: RARalpha
<220> FEATURE:
<221> NAME/KEY: misc_feature
<222> LOCATION: (165)..(666)
<223> OTHER INFORMATION: FrC
<220> FEATURE:
<221> NAME/KEY: misc_feature
<223> OTHER INFORMATION: PML-RAR alpha-FrC construct

<400> SEQUENCE: 7
atggactgga cctggagggt cttctgcttg ctggctgtgg ccccgggggc ccactccgag        60
gtcttcctgc caacagcaa ccacgtggcc agtggcgccg gggaggcagc cattgagacc       120
cagagcagca gttctgaaga datagtgccc agccctccct cgaaaaacct tgattgttgg      180
gtcgacaacg aagaagacat cgatgttatc ctgaaaaagt ctaccattct gaacttggac      240
atcaacaacg atattatctc cgacatctct ggtttcaact cctctgttat cacatatcca      300
gatgctcaat ggtgccggg catcaacggc aaagctatcc acctggttaa caacgaatct      360
tctgaagtta tcgtgcacaa ggccatggac atcgaataca cgacatgtt caacaacttc      420 accgttagct tctggctggc ggttccgaaa gtttctgctt cccacctgga acagtacggc      480
actaacgagt actccatcat cagctctatg aagaaacact ccctgtccat cggctctggt      540
tggtctgttt ccctgaaggg taacaacctg atctggactc tgaaagactc cgcgggcgaa      600
agttcgtcag atcactttcc gcgacctgcc ggacaaagtt caacgcgtac ctggctaaca      660
aatggg                                                                666

<210> SEQ ID NO 8
<211> LENGTH: 105
<212> TYPE: DNA
<213> ORGANISM: Artificial
<220> FEATURE:
<221> NAME/KEY: misc_feature
<223> OTHER INFORMATION: PML-RAR alpha AS

<400> SEQUENCE: 8
cgagggaggg ctgggcacta tctcttcaga actgctgctc tgggtctcaa tggctgcctc        60
cccggcgcca ctggccacgt ggttgctgtt gggcaggaag acctc                      105

<210> SEQ ID NO 9
<211> LENGTH: 1360
```

<212> TYPE: DNA
<213> ORGANISM: Artificial
<220> FEATURE:
<221> NAME/KEY: misc_feature
<223> OTHER INFORMATION: FrC

<400> SEQUENCE: 9

```
atgaaaaacc ttgattgttg ggtcgacaac gaagaagaca tcgatgttat cctgaaaaag     60
tctaccattc tgaacttgga catcaacaac gatattatct ccgacatctc tggtttcaac    120
tcctctgtta tcacatatcc agatgctcaa ttggtgccgg gcatcaacgg caaagctatc    180
cacctggtta caacgaatc ttctgaagtt atcgtgcaca aggccatgga catcgaatac    240
aacgacatgt tcaacaactt caccgttagc ttctggctgc gcgttccgaa agtttctgct    300
tcccacctgg aacagtacgg cactaacgag tactccatca tcagctctat gaagaaacac    360
tccctgtcca tcggctctgg ttggtctgtt ccctgaagg gtaacaacct gatctggact    420
ctgaaagact ccgcgggcga agttcgtcag atcacttcc gcgacctgcc ggacaagttc    480
aacgcgtacc tggctaacaa tgggttttc atcactatca ctaacgatcg tctgtcttct    540
gctaacctgt acatcaacgg cgttctgatg ggctccgctg aaatcactgg tctgggcgct    600
atccgtgagg acaacaacat cactcttaag ctgaaccgtg caacaacaa caaccactac    660
gtatccatcg acaagttccg tatcttctgc aaagcactga cccgaaaga gatcgaaaaa    720
ctgtatacca gctacctgtc tatcaccttc ctgcgtgact tctggggtaa cccgctgcgt    780
tacgacaccg aatattacct gatcccggta gcttctagct ctaaagacgt tcagctgaaa    840
aacatcactg actacatgta cctgacccac gcgccgtcct acactaacgg taaactgaac    900
atctactacc gacgtctgta caacggcctg aaaatcatca tcaaacgcta cactccgaac    960
aacgaaatcg attctttcgt taaatctggt gacttcatca aactgtacgt tcttacaac   1020
aacaacgaac acatcgttgg ttacccgaaa gacggtaacg tctttcaaca acctggacag   1080
aattctgcgt gttggttaca acgctccggg tatcccgctg tacaaaaaa gggaagctgt   1140
taaactgcgt gacctgaaaa cctactctgt tcagctgaaa ctgtacgacg acaaaaacgc   1200
ttctctgggt ctggttggta cccacaacgg tcagatcggt aacgacccga accgtgacat   1260
cctgatcgct tctaactggt acttcaacca cctgaaagac aaaatcctgg ttgcgactg   1320
gtacttcgtt ccgaccgatg aaggttggac caacgactag                        1360
```

<210> SEQ ID NO 10
<211> LENGTH: 1519
<212> TYPE: DNA
<213> ORGANISM: Artificial
<220> FEATURE:
<221> NAME/KEY: misc_feature
<222> LOCATION: (1)..(57)
<223> OTHER INFORMATION: VH1 leader
<220> FEATURE:
<221> NAME/KEY: misc_feature
<222> LOCATION: (58)..(162)
<223> OTHER INFORMATION: PML-RARalphaAS
<220> FEATURE:
<221> NAME/KEY: misc_feature
<222> LOCATION: (163)..(1519)
<223> OTHER INFORMATION: Frc
<220> FEATURE:
<221> NAME/KEY: misc_feature
<223> OTHER INFORMATION: PML-RAR alpha-FrC construct

<400> SEQUENCE: 10

```
atggactgga cctggagggt cttctgcttg ctggctgtgg ccccgggggc ccactcccga     60
```

```
gggagggctg ggcactatct cttcagaact gctgctctgg gtctcaatgg ctgcctcccc       120
ggcgccactg gccacgtggt tgctgttggg caggaagacc tcaaaaacct tgattgttgg       180
gtcgacaacg aagaagacat cgatgttatc ctgaaaaagt ctaccattct gaacttggac       240
atcaacaacg atattatctc cgacatctct ggtttcaact cctctgttat cacatatcca       300
gatgctcaat ggtgccgggg catcaacggc aaagctatcc acctggttaa caacgaatct       360
tctgaagtta tcgtgcacaa ggccatggac atcgaataca cgacatgtt caacaacttc        420 accgttagct tctggctgcg cgttccgaaa gtttctgctt cccacctgga acagtacggc       480
actaacgagt actccatcat cagctctatg aagaaacact cccgtccat cggctctggt        540 tggtctgttt ccctgaaggg taacaacctg atctggactc tgaaagactc cgcgggcgaa       600
gttcgtcaga tcactttccg cgacctgccg gacaagttca acgcgtacct ggctaacaaa       660
tgggttttca tcactatcac taacgatcgt ctgtcttctg ctaacctgta catcaacggc       720
gttctgatgg gctccgctga atcactggt ctgggcgcta tccgtgagga caacaacatc        780
actcttaagc tgaaccgtgg caacaacaac aaccactacg tatccatcga caagttccgt       840
atcttctgca aagcactgaa cccgaaagag atcgaaaaac tgtataccag ctacctgtct       900
atcaccttcc tgcgtgactt ctggggtaac ccgctgcgtt acgacaccga atattacctg       960
atcccggtag cttctagctc taaagacgtt cagctgaaaa acatcactga ctacatgtac      1020
ctgacccacg cgccgtccta cactaacggt aaactgaaca tctactaccg acgtctgtac      1080
aacggcctga aaatcatcat caaacgctac actccgaaca cgaaatcga ttctttcgtt       1140 aaatctggtg acttcatcaa actgtacgtt tcttacaaca caacgaaca catcgttggt       1200 tacccgaaag acggtaacgt cttcaacaa cctggacaga attctgcgtg ttggttacaa       1260
cgctccgggt atcccgctgt acaaaaaaag ggaagctgtt aaactgcgtg acctgaaaac      1320
ctactctgtt cagctgaaac tgtacgacga caaaaacgct tctctgggtc tggttggtac      1380
ccacaacggt cagatcggta acgacccgaa ccgtgacatc ctgatcgctt ctaactggta      1440
cttcaaccac ctgaaagaca aaatcctggg ttgcgactgg tacttcgttc gaccgatga       1500 aggttggacc aacgactag                                                   1519
```

```
<210> SEQ ID NO 11
<211> LENGTH: 537
<212> TYPE: DNA
<213> ORGANISM: Artificial
<220> FEATURE:
<221> NAME/KEY: misc_feature
<222> LOCATION: (1)..(9)
<223> OTHER INFORMATION: Kozak sequence
<220> FEATURE:
<221> NAME/KEY: misc_feature
<222> LOCATION: (10)..(66)
<223> OTHER INFORMATION: BCL1 leader
<220> FEATURE:
<221> NAME/KEY: misc_feature
<222> LOCATION: (67)..(537)
<223> OTHER INFORMATION: ScFvBCL1-FrC
<220> FEATURE:
<221> NAME/KEY: misc_feature
<223> OTHER INFORMATION: ScFvBCL1-FrC construct

<400> SEQUENCE: 11
gccgccacca tgggttggag ctgtatcatc ttctttctgg tagcaacagc tacaggtgtg        60
cactcccagg tccagctgca gcagtctggg cctgaggtgg tgaggcctgg ggtctcagtg       120
aagatttcct gcaagggttc cggctacaca ttcactgatt atgctatgca ctgggtgaag       180
```

```
cagagtcatg caaagagtct agagtggatt ggagttatta gtacttacaa tggtaataca        240
aactacaacc agaagtttaa gggcaaggcc acaatgactg tagacaaatc ctccagcaca        300
gcctatatgg aacttgccag attgacatct gaggattctg ccatctatta ctgtgcaaga        360
tactatggta actactttga ctactggggc caagggacca cggtcaccgt ctcctcaggt        420
ggaggcggtt caggcggagg tggctctggc ggtggcggat cccaggctgt tgggacatgg        480
gccatcgccc tgatagacgg tttttcgccc ttgacgttgg agtccacgtt ctttaat         537

<210> SEQ ID NO 12
<211> LENGTH: 30
<212> TYPE: DNA
<213> ORGANISM: Artificial
<220> FEATURE:
<221> NAME/KEY: misc_feature
<223> OTHER INFORMATION: primer

<400> SEQUENCE: 12
actgctcttc ctcccgaggg agggctgggc                                         30

<210> SEQ ID NO 13
<211> LENGTH: 30
<212> TYPE: DNA
<213> ORGANISM: Artificial
<220> FEATURE:
<221> NAME/KEY: misc_feature
<223> OTHER INFORMATION: primer

<400> SEQUENCE: 13
actgctcttc ctttgaggtc ttcctgccca                                         30
```